(12) United States Patent
Friedman et al.

(10) Patent No.: US 7,521,258 B2
(45) Date of Patent: Apr. 21, 2009

(54) METHODS OF DETECTING, MEASURING, AND EVALUATING MODULATORS OF BODY WEIGHT IN BIOLOGICAL SAMPLES, AND DIAGNOSTIC, MONITORING, AND THERAPEUTIC USES THEREOF

(75) Inventors: Jeffrey M. Friedman, New York, NY (US); Yiying Zhang, New York, NY (US); Ricardo Proenca, Astoria, NY (US)

(73) Assignee: The Rockefeller University, New York, NY (US)

( * ) Notice: Subject to any disclaimer, the term of this patent is extended or adjusted under 35 U.S.C. 154(b) by 330 days.

(21) Appl. No.: 10/780,295

(22) Filed: Feb. 17, 2004

(65) Prior Publication Data

US 2004/0214214 A1  Oct. 28, 2004

Related U.S. Application Data

(62) Division of application No. 09/316,393, filed on May 21, 1999, now Pat. No. 6,734,160, which is a division of application No. 08/292,345, filed on Aug. 17, 1994, now Pat. No. 6,001,968.

(51) Int. Cl.
| | |
|---|---|
| G01N 33/53 | (2006.01) |
| G01N 33/532 | (2006.01) |
| G01N 33/536 | (2006.01) |
| G01N 33/537 | (2006.01) |
| G01N 33/543 | (2006.01) |
| A61K 39/395 | (2006.01) |
| A61K 39/44 | (2006.01) |

(52) U.S. Cl. ............... 436/501; 436/518; 436/538; 530/387.1

(58) Field of Classification Search ............... None
See application file for complete search history.

(56) References Cited

U.S. PATENT DOCUMENTS

| 5,521,283 | A | 5/1996 | DiMarchi et al. |
|---|---|---|---|
| 5,525,705 | A | 6/1996 | DiMarchi et al. |
| 5,532,336 | A | 7/1996 | DiMarchi et al. |
| 5,552,522 | A | 9/1996 | DiMarchi et al. |
| 5,552,523 | A | 9/1996 | Basinski et al. |
| 5,552,524 | A | 9/1996 | Basinski et al. |
| 5,554,727 | A | 9/1996 | Basinski et al. |
| 5,559,208 | A | 9/1996 | Basinski et al. |
| 5,563,243 | A | 10/1996 | DiMarchi et al. |
| 5,563,244 | A | 10/1996 | DiMarchi et al. |
| 5,563,245 | A | 10/1996 | DiMarchi et al. |
| 5,567,678 | A | 10/1996 | DiMarchi et al. |
| 5,567,803 | A | 10/1996 | Basinski et al. |
| 5,569,743 | A | 10/1996 | DiMarchi et al. |
| 5,569,744 | A | 10/1996 | Basinski et al. |
| 5,574,133 | A | 11/1996 | DiMarchi et al. |
| 5,580,954 | A | 12/1996 | DiMarchi et al. |
| 5,594,101 | A | 1/1997 | Becker et al. |
| 5,594,104 | A | 1/1997 | Basinski et al. |
| 5,605,886 | A | 2/1997 | Basinski et al. |
| 5,614,379 | A | 3/1997 | MacKellar et al. |
| 5,643,748 | A | 7/1997 | Snodgrass et al. |
| 5,691,309 | A | 11/1997 | Basinski et al. |
| 5,698,389 | A | 12/1997 | de la Brousse |
| 5,719,266 | A | 2/1998 | DiMarchi et al. |
| 5,827,734 | A | * | 10/1998 | Weigle et al. ............... 435/325 |

FOREIGN PATENT DOCUMENTS

| EP | 725078 A1 | 8/1996 |
|---|---|---|
| EP | 725079 A1 | 8/1996 |
| EP | 736599 A2 | 10/1996 |
| EP | 741187 A2 | 11/1996 |
| EP | 743321 A2 | 11/1996 |
| EP | 744408 A2 | 11/1996 |
| EP | 745610 A2 | 12/1996 |
| EP | 759441 A2 | 2/1997 |
| EP | 764722 A2 | 3/1997 |
| EP | 784979 A2 | 7/1997 |
| EP | 784981 A2 | 7/1997 |
| EP | 784982 A2 | 7/1997 |
| EP | 786256 A2 | 7/1997 |
| EP | 797999 A2 | 10/1997 |
| JP | 8-333394 | 12/1996 |

(Continued)

OTHER PUBLICATIONS

Bahary et al., 1993, Mammalian Genome 4:511-15.

(Continued)

*Primary Examiner*—Christine J Saoud
(74) *Attorney, Agent, or Firm*—Steptoe & Johnson LLP

(57) ABSTRACT

Modulators of weight, including, for example, two isoforms of murine and human ob polypeptides, are provided, as well as diagnostic and therapeutic uses and methods comprising such. Also provided are nucleotide sequences, degenerate variations thereof, and proteins expressed by such. Such materials are useful, for example, as molecular probes, as primers for polymerase chain reaction (PCR) amplification, as well as for the generation of antibodies. Also provided are vectors comprising such nucleotide sequences, including bacterial, insect, and mammalian expression vectors, which nucleotide sequences are operatively associated with an expression control sequence. Cells transformed or transfected with such vectors, and the use of such in the preparation of disclosed modulators, are also provided.

11 Claims, 19 Drawing Sheets

FOREIGN PATENT DOCUMENTS

| | | |
|---|---|---|
| JP | 9-3098 | 1/1997 |
| WO | WO 96/05861 | 2/1996 |
| WO | WO 96/22308 | 7/1996 |
| WO | WO 96/23513 | 8/1996 |
| WO | WO 96/23514 | 8/1996 |
| WO | WO 96/23515 | 8/1996 |
| WO | WO 96/23516 | 8/1996 |
| WO | WO 96/23517 | 8/1996 |
| WO | WO 96/23518 | 8/1996 |
| WO | WO 96/23519 | 8/1996 |
| WO | WO 96/23520 | 8/1996 |
| WO | WO 96/23815 | 8/1996 |
| WO | WO 96/24670 | 8/1996 |
| WO | WO 96/27385 | 9/1996 |
| WO | WO 96/29405 | 9/1996 |
| WO | WO 96/31526 | 10/1996 |
| WO | WO 96/34111 | 10/1996 |
| WO | WO 96/34885 | 11/1996 |
| WO | WO 96/35787 | 11/1996 |
| WO | WO 96/36641 | 11/1996 |
| WO | WO 96/36644 | 11/1996 |
| WO | WO 96/37517 | 11/1996 |
| WO | WO 96/38152 | 12/1996 |
| WO | WO 96/38586 | 12/1996 |
| WO | WO 96/40912 | 12/1996 |
| WO | WO 97/00319 | 1/1997 |
| WO | WO 97/00866 | 1/1997 |
| WO | WO 97/02004 | 1/1997 |
| WO | WO 97/06816 | 2/1997 |
| WO | WO 97/11192 | 3/1997 |
| WO | WO 97/12037 | 4/1997 |
| WO | WO 97/13500 | 4/1997 |
| WO | WO 97/15322 | 5/1997 |
| WO | WO 97/16189 | 5/1997 |
| WO | WO 97/16550 | 5/1997 |
| WO | WO 97/18228 | 5/1997 |
| WO | WO 97/18806 | 5/1997 |
| WO | WO 97/18833 | 5/1997 |
| WO | WO 97/19952 | 6/1997 |
| WO | WO 97/20933 | 6/1997 |
| WO | WO 97/24440 | 7/1997 |
| WO | WO 97/25424 | 7/1997 |
| WO | WO 97/25425 | 7/1997 |
| WO | WO 97/26004 | 7/1997 |
| WO | WO 97/26011 | 7/1997 |
| WO | WO 97/26012 | 7/1997 |
| WO | WO 97/26013 | 7/1997 |
| WO | WO 97/26335 | 7/1997 |
| WO | WO 97/26523 | 7/1997 |
| WO | WO 97/26916 | 7/1997 |
| WO | WO 97/27286 | 7/1997 |
| WO | WO 97/28824 | 8/1997 |
| WO | WO 97/31015 | 8/1997 |
| WO | WO 97/32022 | 9/1997 |
| WO | WO 97/35620 | 10/1997 |
| WO | WO 97/38014 | 10/1997 |
| WO | WO 97/40380 | 10/1997 |
| WO | WO 97/41217 | 11/1997 |
| WO | WO 97/41263 | 11/1997 |
| WO | WO 97/42340 | 11/1997 |
| WO | WO 97/46585 | 12/1997 |
| WO | WO 97/46587 | 12/1997 |

OTHER PUBLICATIONS

Bahary et al., 1993, Genomics 16:113-22.
Friedman and Leibel, 1992, Cell 69:217-20.
Bahary et al., 1992, Genomics 13:761-69.
Friedman et al., 1991, Ann. NY Acad. Sci. 630:100-115.
Friedman et al., 1991, Mammalian Genome 1:130-44.
Friedman et al., 1991, Genomics 11:1054-62.
Moll et al., 1991, Am. J. Hum. Genet. 49:1243-55.
Truett et al., 1991, Proc. Natl. Acad. Sci. USA 88:7806-09.
Walther et al., 1991, Genomics 11:424-34.
Bahary, 1990, Proc. Natl. Acad. Sci. USA 87:8642-46.
Harris, 1990, FASEB J. 4:3310-18.
Leibel et al., 1990, "Genetic variation and nutrition in obesity: Approaches to the molecular genetics of obesity", *World Review of Nutrition and Dietetics*, vol. 63 (Simopoulos, A.P. and Childs, B., eds.), pp. 90-101.
Bray, 1989, Am. J. Clin. Nutr. 50:891-902.
Harris et al., 1987, Diabetes 36:523-34.
Bogardus et al., 1986, N. Engl. J. Med. 315:96-100.
Keesey and Powley, 1986, Ann. Rev. Psychol. 37:109-33.
Coleman, 1978, Diabetologia 14:141-48.
Coleman, 1973, Diabetologia 9:294-98.
Hervey, 1959, J. Physiol. 145:336-52.
Dickie and Lane, 1957, Mouse News Lett. 17:52.
Ingalls et al., 1950, J. Hered. 41:317-18.
Woodworth, J.R., Int. Journal of Obesity Related-Metabolic Disorders, The Pharmacokinetics and Acute Effects of LY355101, A Novel Anitobesity Protein In Healthy Volunteers, vol. 22(3) pp. S63 (1998).
Oral E.A., The New England Journal of Medicine, Leptin-Replacement Theapy for Lipodystrophy, vol. 346:8, pp. 570-578 (Feb. 2002).
Chinookoswong, N., Diabetes, Leptin Restores Euglycenia and Noralizes Glucose Turnover in Insulin-Deficient Diabetes in the Rat, vol. 48, pp. 1-6 (Jul. 1999).

\* cited by examiner

CCAGCAGCTG CAAGGTGCAA GAAGAAGAAG ATCCCAGGGA GGAAAATGTG    50
CTGGAGACCC CTGTGTCGG- TTCCTGTGGC TTTGGTCCTA TCTGTCTTAT   100
GTTCAAGCAG TGCCTATCCA GAAAGTCCAG GATGACACCA AAACCCTCAT   150
CAAGACCATT GTCACCAGGA TCAATGACAT TTCACACACG CAGTCGGTAT   200
CCGCCAAGCA GAGGGTCACT GGCTTGGACT TCATTCCTGG GCTTCACCCC   250
ATTCTGAGTT GTTCCAAGAT GGACCAGACT CTGGCAGTCT ATCAACAGGT   300
CCTCACCAGC CTGCCTTCCC AAAATGTGCT GCAGATAGCC AATGACCTGG   350
AGAATCTCCG AGACCTCCTC CATCTGCTGG CCTTCTCCAA GAGCTGCTCC   400
CTGCCTCAGA CCAGTGGCCT GCAGAAGCCA GAGAGCCTGG ATGGCGTCCT   450
GGAAGCCTCA CTCTACTCCA CAGAGGTGGT GGCTTTGAGC AGGCTGCAGG   500
GCTCTCTGCA GGACATTCTT CAACAGTTGG ATGTTAGCCC TGAATGCTGA   550
AGTTTCAAAG GCCAC-CAGG CTCCAAGAA TCATGTAGAG GGAAGAAACC   600
TTGGCTTCCA GGGGTCTTCA GGA--GAAGA G-AGC-CATG TGCACAC---   650
ATCCA----T CATTCA-TTT CTCTCCCTCC TGTAGACCAC ----CCAT--   700
                                                       701

FIG.1

```
---G--GTTG  CAAGGCCCAA  GAAGCCCA--  -TCCTGGGAA  GGAAAATGCA    50
TTGGGGAACC  CTGTG-CGGA  TTCTTGTGGC  TTTGGCCCTA  TCTTTTCTAT   100
GTCCAAGCTG  TGCCCATCCA  AAAAGTCCAA  GATGACACCA  AAACCCTCAT   150
CAAGACAATT  GTCACCAGGA  TCAATGACAT  TTCACACACG  CAGTCAGTCT   200
CCTCCAAACA  GAAAGTCACC  GGTTTGGACT  TCATTCCTGG  GCTCCACCCC   250
ATCCTGACCT  TATCCAAGAT  GGACCAGACA  CTGGCAGTCT  ACCAACAGAT   300
CCTCACCAGT  ATGCCTTCCA  GAAACGTGAT  CCAAATATCC  AACGACCTGG   350
AGAACCTCCG  GGATCTTCTT  CACGTGCTGG  CCTTCTCTAA  GAGCTGCCAC   400
TTGCCCTGGG  CCAGTGGCCT  GGAGACCTTG  GACAGCCTGG  GGGGTGTCCT   450
GGAAGCTTCA  GGCTACTCCA  CAGAGGTGGT  GGCCCTGAGC  AGGCTGCAGG   500
GGTCTCTGCA  GGACATGCTG  TGGCAGCTGG  ACCTCAGCCC  TGGGTGCTGA   550
GGCCTTGAAG  GTCACTCTTC  CTGCAAGGAC  T-ACGTTAAG  GGAAGGAACT   600
CTGGTTTCCA  GGTATCTCCA  GGATTGAAGA  GCATTGCATG  GACACCCCTT   650
ATCCAGGACT  CTGTCAATTT  CCCTGACTCC  TCTAAGCCAC  TCTTCCAAAG   700
G                                                            701
```

FIG.2

1    Met Cys Trp Arg Pro Leu Cys Arg Phe Leu Trp Leu Trp Ser Tyr
16   Leu Ser Tyr Val Gln Ala Val Pro Ile Gln Lys Val Gln Asp Asp
31   Thr Lys Thr Leu Ile Lys Thr Ile Val Thr Arg Ile Asn Asp Ile
46   Ser His Thr Gln Ser Val Ser Ala Lys Gln Arg Val Thr Gly Leu
61   Asp Phe Ile Pro Gly Leu His Pro Ile Leu Ser Leu Ser Lys Met
76   Asp Gln Thr Leu Ala Val Tyr Gln Gln Val Leu Thr Ser Leu Pro
91   Ser Gln Asn Val Leu Gln Ile Ala Asn Asp Leu Glu Asn Leu Arg
106  Asp Leu Leu His Leu Leu Ala Phe Ser Lys Ser Cys Ser Leu Pro
121  Gln Thr Ser Gly Leu Gln Lys Pro Glu Ser Leu Asp Gly Val Leu
136  Glu Ala Ser Leu Tyr Ser Thr Glu Val Val Ala Leu Ser Arg Leu
151  Gln Gly Ser Leu Gln Asp Ile Leu Gln Gln Leu Asp Val Ser Pro
166  Glu Cys End

FIG.3

1    Met His Trp Gly Thr Leu Cys Gly Phe Leu Trp Leu Trp Pro Tyr
16   Leu Phe Tyr Val Gln Ala Val Pro Ile Gln Lys Val Gln Asp Asp
31   Thr Lys Thr Leu Ile Lys Thr Ile Val Thr Arg Ile Asn Asp Ile
46   Ser His Thr Gln Ser Val Ser Ser Lys Gln Lys Val Thr Gly Leu
61   Asp Phe Ile Pro Gly Leu His Pro Ile Leu Thr Leu Ser Lys Met
76   Asp Gln Thr Leu Ala Val Tyr Gln Gln Ile Leu Thr Ser Met Pro
91   Ser Arg Asn Val Ile Gln Ile Ser Asn Asp Leu Glu Asn Leu Arg
106  Asp Leu Leu His Val Leu Ala Phe Ser Lys Ser Cys His Leu Pro
121  Trp Ala Ser Gly Leu Glu Thr Leu Asp Ser Leu Gly Gly Val Leu
136  Glu Ala Ser Gly Tyr Ser Thr Glu Val Val Ala Leu Ser Arg Leu
151  Gln Gly Ser Leu Gln Asp Met Leu Trp Gln Leu Asp Leu Ser Pro
166  Gly Cys End

FIG.4

```
  1  MET CYS TRP ARG PRO LEU CYS ARG PHE LEU TRP LEU TRP SER TYR
 16  LEU SER TYR VAL GLN ALA VAL PRO ILE GLN LYS VAL GLN ASP ASP
 31  THR LYS THR LEU ILE LYS THR ILE VAL THR ARG ILE ASN ASP ILE
 46  SER HIS THR SER VAL SER ALA LYS GLN ARG VAL THR GLY LEU ASP
 61  PHE ILE PRO GLY LEU HIS PRO ILE LEU SER LEU SER LYS MET ASP
 76  GLN THR LEU ALA VAL TYR GLN GLN VAL LEU THR SER LEU PRO SER
 91  GLN ASN VAL LEU GLN ILE ALA ASN ASP LEU GLU ASN LEU ARG ASP
106  LEU LEU HIS LEU LEU ALA PHE SER LYS SER CYS SER LEU PRO GLN
121  THR SER GLY LEU GLN LYS PRO GLU SER LEU ASP GLY VAL LEU GLU
136  ALA SER LEU TYR SER THR GLU VAL VAL ALA LEU SER ARG LEU GLN
151  GLY SER LEU GLN ASP ILE LEU GLN GLN LEU ASP VAL SER PRO GLU
166  CYS END
```

FIG.5

| | | | | | | | | | | | | | | | |
|---|---|---|---|---|---|---|---|---|---|---|---|---|---|---|---|
| 1 | Met | His | Trp | Gly | Thr | Leu | Cys | Gly | Phe | Leu | Trp | Leu | Trp | Pro | Tyr |
| 16 | Leu | Phe | Tyr | Val | Gln | Ala | Val | Pro | Ile | Gln | Lys | Val | Gln | Asp | Asp |
| 31 | Thr | Lys | Thr | Leu | Ile | Lys | Thr | Ile | Val | Thr | Arg | Ile | Asn | Asp | Ile |
| 46 | Ser | His | Thr | Ser | Val | Ser | Ser | Lys | Gln | Lys | Val | Thr | Gly | Leu | Asp |
| 61 | Phe | Ile | Pro | Gly | Leu | His | Pro | Ile | Leu | Thr | Leu | Ser | Lys | Met | Asp |
| 76 | Gln | Thr | Leu | Ala | Val | Tyr | Gln | Gln | Ile | Leu | Thr | Ser | Met | Pro | Ser |
| 91 | Arg | Asn | Val | Ile | Gln | Ile | Ser | Asn | Asp | Leu | Glu | Asn | Leu | Arg | Asp |
| 106 | Leu | Leu | His | Val | Leu | Ala | Phe | Ser | Lys | Ser | Cys | His | Leu | Pro | Trp |
| 121 | Ala | Ser | Gly | Leu | Glu | Thr | Leu | Asp | Ser | Leu | Gly | Gly | Val | Leu | Glu |
| 136 | Ala | Ser | Gly | Tyr | Ser | Thr | Glu | Val | Val | Ala | Leu | Ser | Arg | Leu | Gln |
| 151 | Gly | Ser | Leu | Gln | Asp | Met | Leu | Trp | Gln | Leu | Asp | Leu | Ser | Pro | Gly |
| 166 | Cys | End | | | | | | | | | | | | | |

FIG.6

```
           +10        +20          +30         +40
GTGCAAGAAG AAGAAGATCC CAGGGCAGGA AAATGTGCTG GAGACCCCTG
---------- ---------- ---------- ---------- ----------
CACGTTCTTC TTCTTCTAGG GTCCCGTCCT TTTACACGAC CTCTGGGGAC

+10        +20          +30         +40
TGTCGGGTCC NGTGGNTTTG GTCCTATCTG TCTTATGTNC AAGCAGTGCC
---------- ?--------- ---------- ---------?- ----------
ACAGCCCAGG NCACCNAAAC CAGGATAGAC AGAATACANG TTCGTCACGG

+10        +20          +30         +40
TATCCAGAAA GTCCAGGATG ACACCAAAAG CCTCATCAAG ACCATTGTCA
---------- ---------- ---------- ---------- ----------
ATAGGTCTTT CAGGTCCTAC TGTGGTTTTC GGAGTAGTTC TGGTAACAGT

+10        +20          +30         +40
NCAGGATCAC TGANATTTCA CACACG
?--------- ---?------ -----
NGTCCTAGTG ACTNTAAAGT GTGTGC
```

FIG. 10

FIG. 14
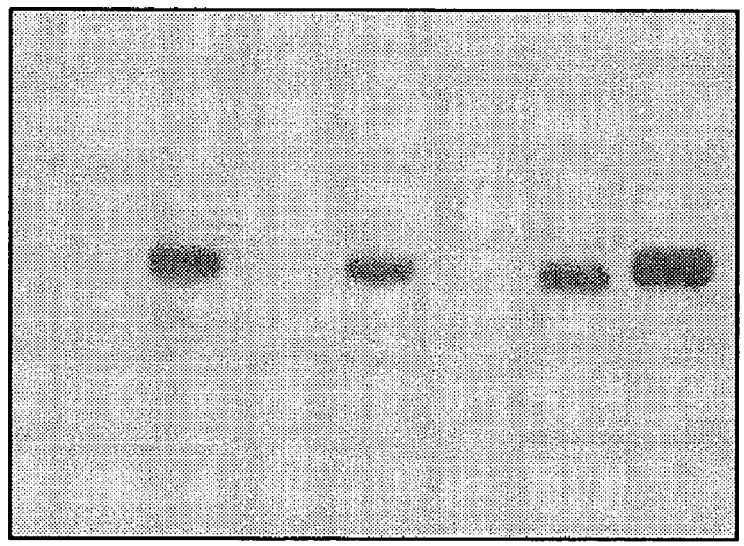
2G7
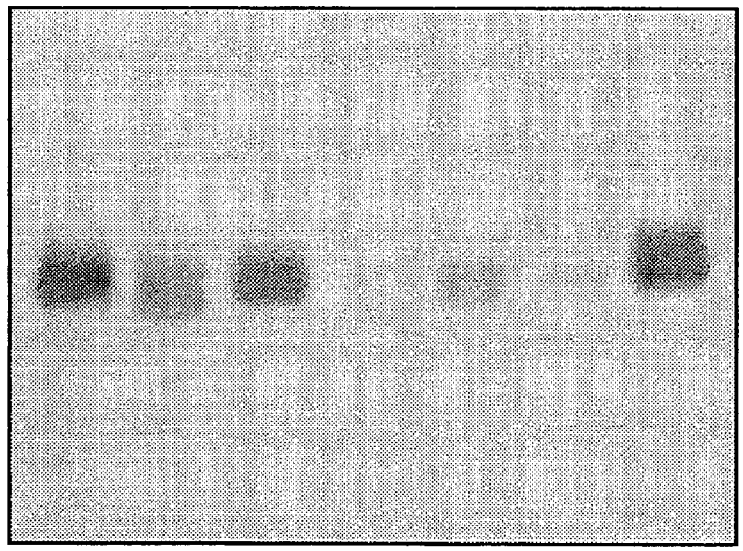
ap2

```
T7 PROMOTER PRIMER 69348-1
------------->
           T7 PROMOTER
------------------->                    LAC OPERATOR         XbaI
BglII                                                        ‾‾‾‾
‾‾‾‾‾
AGATCTCGATCCCGCGAAATTAATACGACTCACTATAGGGGAATTGTGAGCGGATAACAATTCCCCTCTACA

RBS              NcoI                      His•Tag
         ‾‾‾              ‾‾‾‾                      ‾‾‾‾‾‾‾
AATAATTTTGTTTAACTTTAAGAAGGAGATATACCATGGGCAGCAGCCATCATCATCATCATCACAGCAGCGGC
                                     MetGlySerSerHisHisHisHisHisHisSerSerGly

NdeI  XhoI BamHI
           ‾‾‾‾  ‾‾‾‾ ‾‾‾‾‾
CTGGTGCCGCGCGGCAGCCATATGCTCGAGGATCCCGCTGCTAACAAAGCCCGAAAGGAAGCTGAGTTGGCT
LeuValProArgGlySerHisMetLeuGluAspProAlaAlaAlaAsnLysAlaAlaArgLysGluAlaGluLeuAla
THROMBIN
‾‾‾‾‾‾‾‾

BpuI1021                                    T7 TERMINATOR
   ‾‾‾‾‾‾‾‾                                    ‾‾‾‾‾‾‾‾‾‾‾‾‾
GCTGCCACCGCTGAGCAATAACTAGCATAACCCCTTGGGGCCTCTAAACGGGTCTTGAGGGGTTTTTG
AlaAlaThrAlaGluGlnEnd
                <-------------
                T7 TERMINATOR PRIMER #69337-1
```

FIG.19

METHODS OF DETECTING, MEASURING, AND EVALUATING MODULATORS OF BODY WEIGHT IN BIOLOGICAL SAMPLES, AND DIAGNOSTIC, MONITORING, AND THERAPEUTIC USES THEREOF

CROSS REFERENCE TO RELATED APPLICATIONS

The application is a divisional of U.S. patent application Ser. No. 09/316,393, filed May 21, 1999, now U.S. Pat. No. 6,734,160, which is a divisional of U.S. patent application Ser. No. 08/292,345, filed Aug. 17, 1994, now U.S. Pat. No. 6,001,968.

The research leading to the present inventions was funded in part by Grant No. DK 41096 from the National Institutes of Health. The government may have certain rights in the invention.

TECHNICAL FIELD OF THE INVENTION

The present invention relates generally to the control of body weight of mammals including animals and humans, and more particularly to materials identified herein as modulators of weight, and to the diagnostic and therapeutic uses to which such modulators may be put.

BACKGROUND OF THE INVENTION

Obesity, defined as an excess of body fat relative to lean body mass, is associated with important psychological and medical morbidities, the latter including hypertension, elevated blood lipids, and Type II or non-insulin-dependent diabetes melitis (NIDDM). There are 6-10 million individuals with NIDDM in the U.S., including 18% of the population of 65 years of age (Harris et al., 1987). Approximately 45% of males and 70% of females with NIDDM are obese, and their diabetes is substantially improved or eliminated by weight reduction (Harris, 1991). As described below, both obesity and NIDDM are strongly heritable, though the predisposing genes have not been identified. The molecular genetic basis of these metabolically related disorders is an important, poorly understood problem.

The assimilation, storage, and utilization of nutrient energy constitute a complex homeostatic system central to survival of metazoa. Among land-dwelling mammals, storage in adipose tissue of large quantities of metabolic fuel as triglycerides is crucial for surviving periods of food deprivation. The need to maintain a fixed level of energy stores without continual alterations in the size and shape of the organism requires the achievement of a balance between energy intake and expenditure. However, the molecular mechanisms that regulate energy balance remain to be elucidated. The isolation of molecules that transduce nutritional information and control energy balance will be critical to an understanding of the regulation of body weight in health and disease.

An individual's level of adiposity is, to a large extent, genetically determined. Examination of the concordance rates of body weight and adiposity amongst mono- and dizygous twins or adoptees and their biological parents have suggested that the heritability of obesity (0.4-0.8) exceeds that of many other traits commonly thought to have a substantial genetic component, such as schizophrenia, alcoholism, and atherosclerosis (Stunkard et al., 1990). Familial similarities in rates of energy expenditure have also been reported (Bogardus et al., 1986). Genetic analysis in geographically delimited populations has suggested that a relatively small number of genes may account for the 30%-50% of variance in body composition (Moll et al., 1991). However, none of the genes responsible for obesity in the general population have been genetically mapped to a definite chromosomal location.

Rodent models of obesity include seven apparently single-gene mutations. The most intensively studied mousse obesity mutations are the ob (obese) and db (diabetes) genes. When present on the same genetic strain background, ob and db result in indistinguishable metabolic and behavioral phenotypes, suggesting that these genes may function in the same physiologic pathway (Coleman, 1978). Mice homozygous for either mutation are hyperphagic and hypometabolic, leading to an obese phenotype that is notable at one month of age. The weight of these animals tends to stabilize at 60-70 g (compared with 30-35 g in control mice). ob and db animals manifest a myriad of other hormonal and metabolic changes that have made it difficult to identify the primary defect attributable to the mutation (Bray et al., 1989).

Each of the rodent obesity models is accompanied by alterations in carbohydrate metabolism resembling those in Type II diabetes in man. In some cases, the severity of the diabetes depends in part on the background mouse strain (Leiter, 1989). For both ob and db, congenic C57BL/Ks mice develop a severe diabetes with ultimate $\beta$ cell necrosis and islet atrophy, resulting in a relative insulinopenia. Conversely, congenic C57BL/6J ob and db mice develop a transient insulin-resistant diabetes that is eventually compensated by $\beta$ cell hypertrophy resembling human Type II diabetes.

The phenotype of ob and db mice resembles human obesity in ways other than the development of diabetes—the mutant mice eat more and expend less energy than do lean controls (as do obese humans). This phenotype is also quite similar to that seen in animals with lesions of the ventromedial hypothalamus, which suggests that both mutations may interfere with the ability to properly integrate or respond to nutritional information within the central nervous system. Support for this hypothesis comes from the results of parabiosis experiments (Coleman, 1973) that suggest ob mice are deficient in a circulating satiety factor and that db mice are resistant to the effects of the ob factor (possibly due to an ob receptor defect). These experiments have led to the conclusion that obesity in these mutant mice may result from different defects in an afferent loop and/or integrative center of the postulated feedback mechanism that controls body composition.

Using molecular and classical genetic markers, the ob and db genes have been mapped to proximal chromosome 6 and midchromosome 4, respectively (Bahary et al., 1990; Friedman et al., 1991b). In both cases, the mutations map to regions of the mouse genome that are syntonic with human, suggesting that, if there are human homologs of ob and db, they are likely to map, respectively, to human chromosomes 7q and 1p. Defects in the db gene may result in obesity in other mammalian species: in genetic crosses between Zucker falfa rats and Brown Norway +/+ rats, the fa mutation (rat chromosome 5) is flanked by the same loci that flank db in mouse (Truett et al., 1991).

Because of the myriad factors that seem to impact body weight, it is difficult to speculate as to which of these factors, and more particularly, which homeostatic mechanism is actually primarily determinative. Nonetheless, the apparent connection between the ob gene and the extent and characteristics of obesity have prompted the further investigation and elucidation that is reflected by the present application. It is the identification of the sequence of the gene and corresponding peptide materials, to which the present invention following below directs itself.

SUMMARY OF THE INVENTION

In its broadest aspect, the present invention relates to the elucidation and discovery of nucleotide sequences, and proteins putatively expressed by such nucleic acids or degenerate variations thereof, that demonstrate the ability to participate in the control of mammalian body weight. The nucleotide sequences in object are believed to represent the genes corresponding to the murine and human ob gene, that is postulated to play a critical role in the regulation of body weight and adiposity. Preliminary data, presented herein, suggests that the polypeptide product of the gene in question functions as a hormone.

In a first instance, the modulators of the present invention comprise nucleic acid molecules, including recombinant DNA molecules or cloned genes, or degenerate variants thereof, which encode polypeptides themselves serving as modulators of weight control as hereinafter defined, or conserved variants or fragments thereof, which polypeptides possess amino acid sequences such as set forth in FIG. 3 (SEQ ID NO:2), FIG. 4 (SEQ ID NO:4), FIG. 5 (SEQ ID NO:5) and FIG. 6 (SEQ ID NO:6). In specific embodiments, amino acid sequences for two variants of murine and human ob polypeptides are provided. Both polypeptides are found in a form with glutamine 49 deleted, which may result from mRNA splicing.

The nucleic acid molecules, recombinant DNA molecules, or cloned genes, may have the nucleotide sequences or may be complementary to DNA sequences shown in FIG. 1 (SEQ ID NO:1) and FIG. 2 (SEQ ID NO:3). Accordingly, the present invention also relates to the identification of a gene having a nucleotide sequence selected from the sequences of FIG. 1 (SEQ ID NO:1) and FIG. 2 (SEQ ID NO:3) herein, and degenerate variants, allelic variations, and like cognate molecules.

A nucleic acid molecule of the invention can be DNA or RNA, including synthetic variants thereof having phosphate or phosphate analog, e.g., thiophosphate, bonds. Both single stranded and double stranded sequences are contemplated herein.

The present invention further provides nucleic acid molecules for use as molecular probes, or as primers for polymerase chain reaction (PCR) amplification, i.e., synthetic or natural oligonucleotides having a sequence corresponding to a portion of the sequences shown in FIG. 1 (SEQ ID NO:1) and FIG. 2 (SEQ ID NO:3). In particular, the invention contemplates a nucleic acid molecule having at least about 10 nucleotides, wherein a sequence of the nucleic acid molecule corresponds to a nucleotide sequence of the same number of nucleotides in the nucleotide sequences of FIG. 1 (SEQ ID NO:1) or FIG. 2 (SEQ ID NO:3), or a sequence complementary thereto. More preferably, the nucleic acid sequence of the molecule has at least 15 nucleotides. Most preferably, the nucleic acid sequence has at least 20 nucleotides. In an embodiment of the invention in which the oligonucleotide is a probe, the oligonucleotide is detectably labeled, e.g., with a radionuclide (such as $^{32}$P), or an enzyme.

In further aspects, the present invention provides a cloning vector, which comprises the nucleic acids of the invention; and a bacterial, insect, or a mammalian expression vector, which comprises the nucleic acid molecules of the invention, operatively associated with an expression control sequence. Accordingly, the invention further relates to a bacterial cell or a mammalian transfected or transformed with an appropriate expression vector, and correspondingly, to the use of the above mentioned constructs in the preparation of the modulators of the invention.

All of the foregoing materials are to be considered herein as modulators of body weight and fat composition, and as such, may be used in a variety of contexts. Specifically, the invention contemplates both diagnostic and therapeutic applications, as well as certain agricultural applications, all contingent upon the use of the modulators defined herein, including both nucleic acid molecules and peptides. Moreover, the modulation of body weight carries specific therapeutic implications and benefits, in that conditions where either obesity or, conversely, cachexia represent undesired bodily conditions, can be remedied by the administration of one or more of the modulators of the present invention.

Thus, a method for modulating body weight of a mammal is proposed that comprises controlling the expression of the protein encoded by a nucleic acid having nucleotide sequence selected from the sequence of FIG. 1 (SEQ ID NO:1), the sequence of FIG. 2 (SEQ ID NO:3) and degenerate and allelic variants thereof. Such control may be effected by the introduction of the nucleotides in question by gene therapy into fat cells of the patient or host to control or reduce obesity. Conversely, the preparation and administration of antagonists to the nucleotides, such as anti-sense molecules, would be indicated and pursued in the instance where conditions involving excessive weight loss, such as anorexia nervosa, cancer, or AIDS are present and under treatment. Such constructs would be introduced in similar fashion to the nucleotides, directly into fat cells to effect such changes.

Correspondingly, the proteins defined by FIGS. 3, 4, 5, and 6 (SEQ ID NO:1, SEQ ID NO:4, SEQ ID NO:5, and SEQ ID NO:6), conserved variants, active fragments thereof, and cognate small molecules could be formulated for direct administration for therapeutic purposes, to effect reduction or control of excessive body fat or weight gain. Correspondingly, antibodies and other antagonists to the stated protein materials could be prepared and similarly administered to achieve the converse effect. Accordingly, the invention is advantageously directed to a pharmaceutical composition comprising an ob polypeptide of the invention, or alternatively an antagonist thereof, in an admixture with a pharmaceutically acceptable carrier or excipient.

The diagnostic uses of the present nucleotides and corresponding peptides extend to the use of the nucleotides to identify further mutations of allelic variations thereof, so as to develop a repertoire of active nucleotide materials useful in both diagnostic and therapeutic applications. In particular, both homozygous and heterozygous mutations of the nucleotides in question could be prepared that would be postulated to more precisely quantitate the condition of patients, to determine the at-risk potential of individuals with regard to obesity. Specifically, heterozygous mutations are presently viewed as associated with mild to moderate obesity, while homozygous mutations would be associated with a more pronounced and severe obese condition. Corresponding DNA testing could then be conducted utilizing the aforementioned ascertained materials as benchmarks, to facilitate an accurate long term prognosis for particular tendencies, so as to be able to prescribe changes in either dietary or other personal habits, or direct therapeutic intervention, to avert such conditions.

The diagnostic utility of the present invention extends to methods for measuring the presence and extent of the modulators of the invention in cellular samples or extracts taken from test subjects, so that both the encoded nucleotide (RNA) and or the levels of protein in such test samples could be ascertained. Given that the increased activity of the nucleotide and presence of the resulting protein reflect the capability of the subject to inhibit obesity, the physician reviewing such results in an obese subject would determine that a factor other than dysfunction with respect to the presence and activity of the nucleotides of the present invention is a cause of the obese condition. Conversely, depressed levels of the nucleotide and or the expressed protein would suggest that such levels must be increased to treat such obese condition, and an appropriate therapeutic regimen could then be implemented.

Further, the nucleotides discovered and presented in FIGS. 1 and 2 represent cDNA in which, as stated briefly above, is useful in the measurement of corresponding RNA. Likewise, recombinant protein material corresponding to the polypeptides of FIGS. 3 and 4 may be prepared and appropriately labeled, for use, for example, in radioimmunoassays, for example, for the purpose of measuring fat and or plasma levels of the ob protein.

The invention further directs itself recombinant DNA molecules comprising the DNA sequences of FIGS. 1 and 2, which molecules are in a further embodiment operatively linked to an expression control sequence. Suitable expression control sequences may be selected from among those presently and generally available and in use. The invention further extends to probes prepared from the sequences of FIG. 1 or 2 and to hosts transformed with recombinant DNA molecules prepared in accordance with the present invention.

Yet further, the present invention contemplates not only the identification of the nucleotides and corresponding proteins presented herein, but the elucidation of the receptor to such materials. In such context, the polypeptides of FIGS. 3, 4, 5, and/or 6 could be prepared and utilized to screen an appropriate expression library to isolate active receptors. The receptor could thereafter be cloned, and the receptor alone or in conjunction with the ligand could thereafter be utilized to screen for small molecules that may possess like activity to the modulators herein.

Yet further, the present invention relates to pharmaceutical compositions that include certain of the modulators hereof, preferably the polypeptides whose sequences are presented in SEQ ID NO:2, SEQ ID NO:4, SEQ ID NO:5 and SEQ ID NO:6, their antibodies, corresponding small molecules exhibiting either antagonism or mimicry, or active fragments prepared in formulations for a variety of modes of administration, where such therapy is appropriate. Such formulations would include pharmaceutically acceptable carriers, or other adjuvants as needed, and would be prepared in effective dosage ranges to be determined by the clinician or the physician in each instance.

Accordingly, it is a principal object of the present invention to provide modulators of body weight as defined herein in purified form, that exhibit certain characteristics and activities associated with control and variation of adiposity and fat content of mammals.

It is a further object of the present invention to provide methods for the detection and measurement of the modulators of weight control as set forth herein, as a means of the effective diagnosis and monitoring of pathological conditions wherein the variation in level of such modulators is or may be a characterizing feature.

It is a still further object of the present invention to provide a method and associated assay system for the screening of substances, such as drugs, agents and the like, that are potentially effective to either mimic or inhibit the activity of the modulators of the invention in mammals.

It is a still further object of the present invention to provide a method for the treatment of mammals to control body weight and fat content in mammals, and or to treat certain of the pathological conditions of which abnormal depression or elevation of body weight is a characterizing feature.

It is a still further object of the present invention to prepare genetic constructs for use in genetic therapeutic protocols and or pharmaceutical compositions for comparable therapeutic methods, which comprise or are based upon one or more of the modulators, binding partners, or agents that may control their production, or that may mimic or antagonize their activities.

Other objects and advantages will become apparent to those skilled in the art from a review of the ensuing description which proceeds with reference to the following illustrative drawings.

BRIEF DESCRIPTION OF THE DRAWINGS

FIG. 1 depicts the nucleic acid sequence derived for the murine ob gene. The nucleotides are numbered from 1 to 701 with a start site at nucleotide 46 and a termination at nucleotide 550.

FIG. 2 depicts the nucleic acid sequence derived for the human ob gene. The nucleotides are numbered from 1 to 701 with a start site at nucleotide 46 and a termination at nucleotide 550.

FIG. 3 depicts the full deduced amino acid sequence derived for the murine ob gene corresponding to the nucleic acid sequence of FIG. 1. The nucleotides are numbered from 1 to 167. A signal sequence cleavage site is located after amino acid 21 (Ala) so that the mature protein extends from amino acid 22 (Val) to amino acid 167 (Cys).

FIG. 4 depicts the full deduced amino acid sequence derived for the human ob gene corresponding to the nucleic acid sequence of FIG. 2. The amino acids are numbered from 1 to 167. A signal sequence cleavage site is located after amino acid 21 (Ala) so that the mature protein extends from amino acid 22 (Val) to amino acid 167 (Cys).

FIG. 5 depicts the full length amino acid sequence (SEQ ID NO:5) derived for the murine ob gene as shown in FIG. 3, but lacking glutamine at position 49. The nucleotides are numbered from 1 to 166. A signal sequence cleavage site is located after amino acid 21 (Ala) (and thus, before the glutamine 49 deletion) so that the mature protein extends from amino acid 22 (Val) to amino acid 166 (Cys).

FIG. 6 depicts the full deduced amino acid sequence (SEQ ID NO:6) derived for the human ob gene as shown in FIG. 4, but lacking glutamine at position 49. The nucleotides are numbered from 1 to 166. A signal sequence cleavage site is located after amino acid 21 (Ala) (and thus, before the glutamine 49 deletion) so that the mature protein extends from amino acid 22 (Val) to amino acid 166 (Cys).

FIG. 10 presents the sequence of the 2G7 clone, which includes an exon coding for a part of the ob gene. The primer sequences used to amplify this exon are boxed in the figure.

FIG. 14 is a Northern analysis of 2J animals and control animals that confirms the absence of the ob mRNA from 2J animals. The Northern analysis was performed as in FIGS. 11 and 13. In this case, the control RNA was ap2, a fat specific transcript. There is no significance to the varying density of the ap2 bands.

FIG. 19 presents the expression cloning region of vector pET-15b (Novagen).

DETAILED DESCRIPTION

Figure 7:
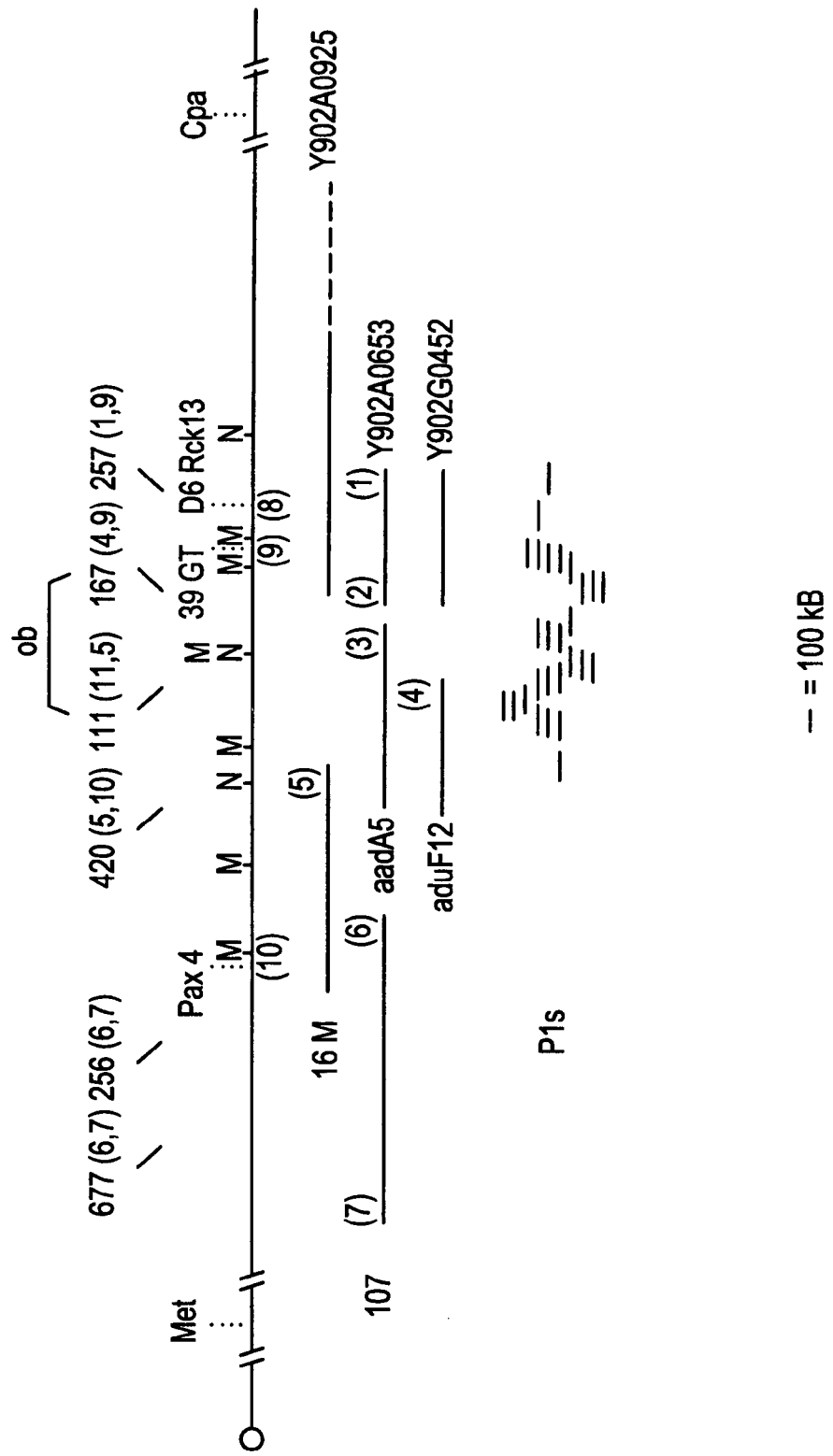
FIG. 7 presents a physical map of the location of ob in the murine chromosome, and the YAC and P1 cloning maps. "M and N" corresponds to MuII and NotI restriction sites. The numbers that are followed by parentheses correspond to individual animals that were recombinant in the region of ob. Ignore the numbers in parentheses. 39gt, Pax-4, D6 Drck13 cp2, and met, refer to locations in the region of ob that bind to the DNA probes. (A) The top series of lines is a schematic map corresponding to a region of the chromosome. (B) The next series of lines corresponds to YACs (yeast artificial chromosomes) from the region. (C) The bottom lines correspond to P1 clones from the region.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

Therefore, if appearing herein, the following terms shall have the definitions set out below.

The term "body weight modulator", "modulator", "modulators", and any variants not specifically listed, may be used herein interchangeably, and as used throughout the present application and claims refers in one instance to both nucleotides and to proteinaceous material, the latter including both single or multiple proteins. More specifically, the aforementioned terms extend to the nucleotides and to the DNA having the sequences described herein and presented in FIG. 1 (SEQ ID NO: 1), and FIG. 2 (SEQ ID NO:3). Likewise, the proteins having the amino acid sequence data described herein and presented in FIG. 3 (SEQ ID NO:2), and FIG. 4 (SEQ ID NO:4) are likewise contemplated, as are the profile of activities set forth with respect to all materials both herein and in the claims. Accordingly, nucleotides displaying substantially equivalent or altered activity are likewise contemplated, including substantially homologous analogs and allelic variations. Likewise, proteins displaying substantially equivalent or altered activity, including proteins modified deliberately, as for example, by site-directed mutagenesis, or accidentally through mutations in hosts that produce the modulators are likewise contemplated.

A "replicon" is any genetic element (e.g., plasmid, chromosome, virus) that functions as an autonomous unit of DNA replication in vivo, i.e., capable of replication under its own control.

A "vector" is a replicon, such as a plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

"Heterologous" DNA refers to DNA not naturally located in the cell, or in a chromosomal site of the cell. Preferably, the heterologous DNA includes a gene foreign to the cell.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; more preferably at least about 15 nucleotides; most preferably the length is at least about 20 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is also used herein to refer to this sort of signal sequence. Translocation signal sequences can be found associated with a variety of proteins native to eukaryotes and prokaryotes, and are often functional in both types of organisms.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The term "standard hybridization conditions" refers to salt and temperature conditions substantially equivalent to 5×SSC and 65° C. for both hybridization and wash.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and Fr (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

A composition comprising "A" (where "A" is a single protein, DNA molecule, vector, recombinant host cell, etc.) is substantially free of "B" (where "B" comprises one or more contaminating proteins, DNA molecules, vectors, etc., but excluding racemic forms of A) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology*, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

In its primary aspect, the present invention is directed to the identification of materials that function as modulators of mammalian body weight. In particular, the invention concerns the isolation, purification and sequencing of certain nucleic acids that correspond to the ob gene in both mice and humans, as well as the corresponding polypeptides expressed by these nucleic acids. The invention thus comprises the discovery of nucleic acids having the nucleotide sequences set forth in FIG. 1 (SEQ ID NO:1) and FIG. 2 (SEQ ID NO:3), and to degenerate variants, alleles and fragments thereof, all possessing the activity of modulating body weight and adiposity. The correspondence of the present nucleic acids to the ob gene portends their significant impact on conditions such as obesity as well as other maladies and dysfunctions where abnormalities in body weight are a contributory factor. The invention extends to the proteins expressed by the nucleic acids of the invention, and particularly to those proteins set forth in FIG. 3 (SEQ ID NO:2), FIG. 4 (SEQ ID NO:4), FIG. 5 (SEQ ID NO:5), and FIG. 6 (SEQ ID NO:6), as well as conserved variants, active fragments, and cognate small molecules.

In particular, the present invention contemplates that naturally occurring fragments of the ob polypeptide may be important. The peptide sequence includes a number of sites that are frequently the target for proteolytic cleavage, e.g., arginine residues. It is possible that the full length polypeptide may be cleaved at one or more such sites to form biologically active fragments. Such biologically active fragments may either agonize or antagonize the functional activity of the ob polypeptide to reduce body weight.

As discussed earlier, the weight control modulator peptides or their binding partners or other ligands or agents exhibiting either mimicry or antagonism to them or control over their production, may be prepared in pharmaceutical compositions, with a suitable carrier and at a strength effective for administration by various means to a patient experiencing abnormal fluctuations in body weight or adiposity, either alone or as part of an adverse medical condition such as cancer or AIDS, for the treatment thereof. A variety of administrative techniques may be utilized, among them parenteral techniques such as subcutaneous, intravenous and intraperitoneal injections, catheterizations and the like. Average quantities of the recognition factors or their subunits may vary and in particular should be based upon the recommendations and prescription of a qualified physician or veterinarian.

Also, antibodies including both polyclonal and monoclonal antibodies, and drugs that modulate the production or activity of the weight control modulators recognition factors and/or their subunits may possess certain diagnostic applications and may for example, be utilized for the purpose of detecting and/or measuring conditions where abnormalities in body weight are or may be likely to develop. For example, the modulator peptides or their active fragments may be used to produce both polyclonal and monoclonal antibodies to themselves in a variety of cellular media, by known techniques such as the hybridoma technique utilizing, for example, fused mouse spleen lymphocytes and myeloma cells. These techniques are described in detail below. Likewise, small molecules that mimic or antagonize the activity (ies) of the receptor recognition factors of the invention may be discovered or synthesized, and may be used in diagnostic and/or therapeutic protocols.

Panels of monoclonal antibodies produced against modulator peptides can be screened for various properties; i.e., isotype, epitope, affinity, etc. Of particular interest are monoclonal antibodies that neutralize the activity of the modulator peptides. Such monoclonals can be readily identified in activity assays for the weight modulators. High affinity antibodies are also useful when immunoaffinity purification of native or recombinant modulator is possible.

Preferably, the anti-modulator antibody used in the diagnostic and therapeutic methods of this invention is an affinity purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

As suggested earlier, a diagnostic method useful in the present invention comprises examining a cellular sample or medium by means of an assay including an effective amount of an antagonist to a modulator protein, such as an anti-modulator antibody, preferably an affinity-purified polyclonal antibody, and more preferably a mAb. In addition, it is preferable for the anti-modulator antibody molecules used herein be in the form of Fab, Fab', F(ab')$_2$ or F(v) portions or whole antibody molecules. As previously discussed, patients capable of benefiting from this method include those suffering from cancer, AIDS, obesity or other condition where abnormal body weight is a characteristic or factor. Methods for isolating the modulator and inducing anti-modulator antibodies and for determining and optimizing the ability of anti-modulator antibodies to assist in the examination of the target cells are all well-known in the art.

The nucleic acids contemplated by the present invention extend as indicated, to other nucleic acids that code on expression for peptides such as those set forth in FIG. 3 (SEQ ID NO:2), FIG. 4 (SEQ ID NO:4), FIG. 5 (SEQ ID NO:5), and FIG. 6 (SEQ ID NO:6) herein. Accordingly, while specific DNA has been isolated and sequenced in relation to the ob gene, any animal cell potentially can serve as the nucleic acid source for the molecular cloning of a gene encoding the peptides of the invention. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired ob or ob-like gene may be accomplished in a number of ways. For example, if an amount of a portion of a ob or ob-like gene or its specific RNA, or a fragment thereof, is available and can be purified and labeled, the generated DNA fragments may be screened by nucleic acid hybridization to the labeled probe (Benton and Davis, 1977, *Science* 196:180; Grunstein and Hogness, 1975, *Proc. Natl. Acad. Sci., U.S.A.* 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in FIG. 1 (SEQ ID NO:1) or FIG. 2 (SEQ ID NO:3). Preferably, a fragment is selected that is highly unique to the modulator peptides of the invention. Those DNA fragments with substantial homology to the probe will hybridize. As noted above, the greater the degree of homology, the more stringent hybridization conditions can be used. In a specific embodiment, low stringency hybridization conditions are used to identify a homologous modulator peptide. However, in a preferred aspect, a nucleic acid encoding a modulator peptide of the invention will hybridize to a nucleic acid having a nucleotide sequence such as depicted in FIG. 1 (SEQ ID NO: 1) or FIG. 2 (SEQ ID NO:3), or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, tyrosine phosphatase activity or antigenic properties as known for the present modulator peptides. For example, the antibodies of the instant invention can conveniently be used to screen for homologs of modulator peptides from other sources.

A gene encoding a modulator peptide of the invention can also be identified by mRNA selection, i.e., by nucleic acid hybridization followed by in vitro translation. In this procedure, fragments are used to isolate complementary mRNAs by hybridization. Such DNA fragments may represent available, purified modulator DNA. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against a modulator peptide.

A radiolabeled modulator peptide cDNA can be synthesized using the selected mRNA (from the adsorbed polysomes) as a template. The radiolabeled mRNA or cDNA may then be used as a probe to identify homologous modulator peptide DNA fragments from among other genomic DNA fragments.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and Synthetic DNA sequences. Suitable vectors include derivatives of SV40 and known bacterial plasmids, e.g., E. coli plasmids col E1, pCR1, pBR322, pMB9, pUC or pUC plasmid derivatives, e.g., pGEX vectors, pmal-c, pFLAG, etc., and their derivatives, plasmids such as RP4; phage DNAs, e.g., the numerous derivatives of phage λ, e.g., NM989, and other phage DNA, e.g., M13 and Filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

In a specific embodiment, an ob fusion protein can be expressed. An ob fusion protein comprises at least a functionally active portion of a non-ob protein joined via a peptide bond to at least a functionally active portion of an ob polypeptide. The non-ob sequences can be amino- or carboxy-terminal to the ob sequences. More preferably, for stable expression of a proteolytically inactive ob fusion protein, the portion of the non-ob fusion protein is joined via a peptide bond to the amino terminus of the ob protein. A recombinant DNA molecule encoding such a fusion protein comprises a sequence encoding at least a functionally active portion of a non-ob protein joined in-frame to the ob coding sequence, and preferably encodes a cleavage site for a specific protease, e.g., thrombin or Factor Xa, preferably at the ob-non-ob juncture. In a specific embodiment, the fusion protein is expressed in *Escherichia coli*.

In a specific embodiment, infra, vectors were prepared to express the murine and human ob genes, with and without the codon for gln-49, in bacterial expression systems as fusion proteins. The ob gene is prepared with an endonuclease cleavage site, e.g., using PCR and novel primers. It is desirable to confirm sequences generated by PCR, since the probability of including a point mutation is greater with this technique. A plasmid containing a histidine tag (HIS-TAG) and a proteolytic cleavage site is used. The presence of the histidine makes possible the selective isolation of recombinant proteins on a Ni-chelation column, or by affinity purification. The proteolytic cleavage site, in a specific embodiment, infra, a thrombin cleavage site, is engineered so that treatment with the protease, e.g., thrombin, will release the full length mature (i.e., lacking a signal sequence) ob polypeptide.

In another aspect, the gex vector (Smith and Johnson, 1988, Gene 67:31-40) can be used. This vector fuses the schistosoma japonicum glutathionine S-transferase cDNA to the sequence of interest. Bacterial proteins are harvested and recombinant proteins can be quickly purified on a reduced glutathione affinity column. The GST carrier can subsequently be cleaved from fusion proteins by digestion with site-specific proteases. After cleavage, the carrier and uncleaved fusion protein can be removed by absorption on glutathione agarose. Difficulty with the system occasionally arises when the encoded protein is insoluble in aqueous solutions.

In addition to the specific example, the present inventors contemplate use of baculovirus, mammalian, and yeast expression systems to express the ob protein. For example, in baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)).

Mammalian expression vectors contemplated for use in the invention include vectors with inducible promoters, such as dihydrofolate reductase (DHFR), e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12, 1991). Alternatively, a glutamine synthetase/methionine sulfoximine co-amplification vector, such as pEE14 (HindIII, XbaI, SmaI, SmaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker; Invitrogen), pREP8 (BamH1, XhoI, NotI, HindIII, NheI, and KpnI cloning site, RSV LTR promoter, histidinol selectable marker; Invitrogen), pREP9 (KpnI, NheI, HindIII, NotI, XhoI, SfiI, and BamHI cloning site, RSV LTR promoter, G418 selectable marker; Invitrogen), and pEBVHis (RSV LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and HpA cloning site, TK or XPRT selection).

Yeast expression systems can also be used according to the invention to express ob polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

It is further intended that body weight modulator peptide analogs may be prepared from nucleotide sequences derived within the scope of the present invention. Analogs, such as fragments, may be produced, for example, by pepsin digestion of weight modulator peptide material. Other analogs, such as muteins, can be produced by standard site-directed mutagenesis of weight modulator peptide coding sequences. Analogs exhibiting "weight modulator activity" such as small molecules, whether functioning as promoters or inhibitors, may be identified by known in vivo and/or in vitro assays.

As mentioned above, a DNA sequence encoding weight modulator peptides as disclosed herein can be prepared synthetically rather than cloned. The DNA sequence can be designed with the appropriate codons for the weight modulator peptide amino acid sequences. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express weight modulator analogs or "muteins". Alternatively, DNA encoding muteins can be made by site-directed mutagenesis of native modulator genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method may be used to create analogs of the ob polypeptide with unnatural amino acids.

The present invention extends to the preparation of antisense nucleotides and ribozymes that may be used to interfere with the expression of the weight modulator proteins at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (See Weintraub, 1990; Marcus-Sekura, 1988). In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into weight modulator peptide-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, *Tetrahymena*-type and "hammerhead"-type (Hasselhoff and Gerlach, 1988). *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for weight modulator proteins and their ligands.

The present invention also relates to a variety of diagnostic applications, including methods for detecting the presence of conditions and/or stimuli that impact abnormalities in body weight or adiposity, by reference to their ability to elicit the activities which are mediated by the present weight modulators. As mentioned earlier, the weight modulator peptides can be used to produce antibodies to themselves by a variety of known techniques, and such antibodies could then be isolated and utilized as in tests for the presence of particular transcriptional activity in suspect target cells.

Antibody(ies) to the body weight modulators, i.e., the ob polypeptide, can be produced and isolated by standard methods including the well known hybridoma techniques. For convenience, the antibody(ies) to the weight modulators will be referred to herein as $Ab_1$ and antibody(ies) raised in another species as $Ab_2$.

According to the invention, ob polypeptide produced recombinantly or by chemical synthesis, and fragments or other derivatives or analogs thereof, including fusion proteins, may be used as an immunogen to generate antibodies that recognize the ob polypeptide. Such antibodies include but are not limited to polyclonal, monoclonal, chimeric, single chain, Fab fragments, and an Fab expression library.

Various procedures known in the art may be used for the production of polyclonal antibodies to ob polypeptide a recombinant PTP or derivative or analog thereof. For the production of antibody, various host animals can be immunized by injection with the ob polypeptide, or a derivative (e.g., fragment or fusion protein) thereof, including but not limited to rabbits, mice, rats, sheep, goats, etc. In one embodiment, the ob polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the ob polypeptide, or fragment, analog, or derivative thereof, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for an ob polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce ob polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for an ob polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an ob polypeptide, one may assay generated hybridomas for a product which binds to an ob polypeptide fragment containing such epitope. For selection of an antibody specific to an ob polypeptide from a particular species of animal, one can select on the basis of positive binding with ob polypeptide expressed by or isolated from cells of that species of animal.

The foregoing antibodies can be used in methods known in the art relating to the localization and activity of the ob polypeptide, e.g., for Western blotting, imaging ob polypeptide in situ, measuring levels thereof in appropriate physiological samples, etc.

In a specific embodiment, antibodies that agonize or antagonize the activity of ob polypeptide can be generated. Such antibodies can be tested using the assays described infra for identifying ligands.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the gex vector can be used to express the polypeptide (Smith and Johnson, supra). Alternatively, one can use only hydrophilic domains to generate the fusion protein. The expressed protein will be prepared in quantity and used to immunize rabbits in Freunds adjuvant.

The presence of weight modulator in cells can be ascertained by the usual immunological procedures applicable to such determinations. A number of useful procedures are known. Three such procedures which are especially useful utilize either the receptor recognition factor labeled with a detectable label, antibody $Ab_1$ labeled with a detectable label, or antibody $Ab_2$ labeled with a detectable label. The procedures may be summarized by the following equations wherein the asterisk indicates that the particle is labeled, and "WM" stands for the weight modulator:

$$WM^* + Ab_1 = WM^*Ab_1 \qquad \text{A.}$$

$$WM + Ab^* = WMAb_1^* \qquad \text{B.}$$

$$WM + Ab_1 + Ab_2^* = WMAb_1Ab_2^* \qquad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the weight modulators form complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-weight modulator antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The weight modulators or their binding partners can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system that is to be utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the weight modulator may be radiolabeled and combined, for example, with antibodies or other inhibitors thereto, after which binding studies would be carried out. Solutions would then be prepared that contain various quantities of labeled and unlabeled uncombined weight modulator, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic. In turn, a receptor assay will be particularly useful in the identification of the specific receptors to the present modulators, such as the receptor present on db.

A further assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined transcriptional activity or predetermined transcriptional activity capability in suspected target cells. In accordance with the testing techniques discussed above, one class of such kits will contain at least the labeled weight modulator or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for predetermined transcriptional activity, comprising:
(a) a predetermined amount of at least one labeled immunochemically reactive component obtained by the direct or indirect attachment of the present weight modulator or a specific binding partner thereto, to a detectable label;
(b) other reagents; and
(c) directions for use of said kit.

More specifically, the diagnostic test kit may comprise:
(a) a known amount of the weight modulator as described above (or a binding partner) generally bound to a solid phase to form an immunosorbent, or in the alternative, bound to a suitable tag, or plural such end products, etc. (or their binding partners) one of each;
(b) if necessary, other reagents; and
(c) directions for use of said test kit.

In a further variation, the test kit may be prepared and used for the purposes stated above, which operates according to a predetermined protocol (e.g. "competitive", "sandwich", "double antibody", etc.), and comprises:
(a) a labeled component which has been obtained by coupling the weight modulator to a detectable label;
(b) one or more additional immunochemical reagents of which at least one reagent is a ligand or an immobilized ligand, which ligand is selected from the group consisting of:
 (i) a ligand capable of binding with the labeled component (a);
 (ii) a ligand capable of binding with a binding partner of the labeled component (a);
 (iii) a ligand capable of binding with at least one of the component(s) to be determined; and
 (iv) a ligand capable of binding with at least one of the binding partners of at least one of the component(s) to be determined; and
(c) directions for the performance of a protocol for the detection and/or determination of one or more components of an immunochemical reaction between the weight modulator and a specific binding partner thereto.

In accordance with the above, an assay system for screening potential drugs effective to mimic or antagonize the activity of the weight modulator may be prepared. The weight modulator may be introduced into a test system, and the prospective drug may also be introduced into the resulting cell culture, and the culture thereafter examined to observe any changes in the activity of the cells, due either to the addition of the prospective drug alone, or due to the effect of added quantities of the known weight modulator.

As stated earlier, the molecular cloning of the ob gene described herein has led to the identification of a class of materials that function on the molecular level to modulate mammalian body weight. The discovery of the modulators of the invention has important implications for the diagnosis and treatment of nutritional disorders including, but not limited to, obesity, weight loss associated with cancer and the treatment of diseases associated with obesity such as hypertension, heart disease and Type II diabetes. In addition, there are potential agricultural uses for the gene product in cases where one might wish to modulate the body weight of domestic animals. Finally, to the extent that one or more of the modulators of the invention are secreted molecules, they can be used biochemically to isolate their receptor using the technology of expression cloning. The discussion that follows with specific reference to the ob gene bears general applicability to the class of modulators that a part of the present invention, and is therefore to be accorded such latitude and scope of interpretation.

Therapeutic Implications

In the simplest analysis the ob gene determines body weight in mammals, in particular mice and man. The ob gene and, correspondingly, cognate molecules, appear to be part of a signaling pathway by which adipose tissue communicates with the brain and the other organs. It is believed that the ob polypeptide is itself a signaling molecule, i.e., a hormone. Alternatively ob may be responsible for the generation of a metabolic signal, e.g., an enzyme that catalyzes the synthesis of a peptide or steroid hormone. The most important piece of information for distinguishing between these possibilities or considering alternative hypothesis, is the complete DNA sequence of the RNA and its predicted protein sequence. Irrespective of its biochemical function the genetic data suggest that increased activity of ob would result in weight loss while decreased activity would be associated with weight gain. The means by which the activity of ob can be modified so as to lead to a therapeutic effect depends on its biochemical function.

Administration of recombinant ob polypeptide is believed to result in weight loss. Recombinant protein can be prepared using standard bacterial and/or mammalian expression vectors, all as stated in detail earlier herein. Reduction of ob polypeptide activity (by developing antagonists, inhibitors, or antisense molecules) should result in weight gain as might be desirable for the treatment of the weight loss associated with cancer, AIDS or anorexia nervosa. Modulation of ob activity can be useful for reducing body weight (by increasing its activity) or increasing body weight (by decreasing its activity).

For example, the ob gene could be introduced into human fat cells to develop gene therapy for obesity. Such therapy would be expected to decrease body weight. Conversely, introduction of antisense constructs into human fat cells would reduce the levels of active ob polypeptide and would be predicted to increase body adiposity.

If ob is an enzyme, strategies have begun to be developed for the identification of the substrate and product of the catalyzed reaction that would make use of the recombinant protein. The rationale for this strategy is as follows: If ob is an enzyme that catalyzes a particular reaction in adipose tissue, then fat cells from ob mice should have high levels of the substrate and very little product. Since it is hypothesized that db mice are resistant to the product of this reaction, fat cells from db mice should have high levels of the reaction product. Thus, comparisons of lipid and peptide extracts of ob and db adipose tissue using gas chromatography or other chromatographic methods should allow the identification of the product and substrate of the key chemical reaction. The prediction would be that the recombinant ob protein would catalyze this reaction. The product of this reaction would then be a candidate for a signaling molecule that modulates body weight.

The functional activity of the ob polypeptide, and therapeutic uses thereof, can be determined using transgenic mice. Candidate genes less than ~40 kb can be used in complementation studies employing transgenic mice. Transgenic vectors, including viral vectors, or cosmid clones (or phage clones) corresponding to the wild type locus of candidate gene, can be constructed using the isolated YACs as starting material. Cosmids may be introduced into transgenic mice using published procedures (Jaenisch, *Science* 240, 1468-1474, 1988). The constructs are introduced into fertilized eggs derived from an intercross between F1 progeny of a C57BL/6J ob/ob X DBA intercross. These crosses require the use of C57BL/6J ob/ob ovarian transplants to generate the F1 animals. DBA/2J mice are used as the counterstrain because they have a nonagouti coat color which is important when using the ovarian transplants. Genotype at the ob loci in cosmid transgenic animals can be determined by typing animals with tightly linked RFLPs or microsatellites which flank the mutation and which are polymorphic between the progenitor strains. Complemention will be demonstrated when a particular construct renders a genetically obese F2 animal (as scored by RFLP analysis) lean and nondiabetic. Under these circumstances, final proof of complementation will require that the ob/ob or db/db animal carrying the transgene be mated to the ob/ob or db/db ovarian transplants. In this cross, all N2 animals which do not carry the transgene will be obese and insulin resistant/diabetic, while those that do carry the transgene will be lean and have normal glucose and insulin concentrations in plasma. In a genetic sense, the transgene acts as a suppressor mutation. Alternatively, ob genes can be tested by examining their phenotypic effects when express in antisense orientation in wild-type animals. In this approach, expression of the wild type allele is suppressed, which leads to a mutant phenotype. RNARNA duplex formation (antisensesense) prevents normal handling of mRNA, resulting in partial or complete elimination of wild-type gene effect. This technique has been used to inhibit Tk synthesis in tissue culture and to produce phenotypes of the Kruppel mutation in *Drosophila,* and the shiverer mutation in mice (Izant and Weintraub, *Cell* 36, 1007-1015, 1984; Green et al., *Annu. Rev. Biocheni.* 55, 569-597, 1986; Katsuki et al., *Science* 241, 593-595, 1988). An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 poly A site. This transgene will be used to make transgenic mice. Transgenic mice will also be mated ovarian transplants to test whether ob heterozygotes are more sensitive to the effects of the antisense construct.

In the long term, the elucidation of the biochemical function of the ob protein/gene product should also be useful for identifying small molecule agonists and antagonists that affect its activity.

Diagnostic Implications

The human cDNA clones that have recently been isolated have been sequenced as presented herein. This facilitates the determination of the complete sequence of the human gene. It is also proposed to generate DNA sequences from the introns of the human ob gene. This will make it possible to generate DNA sequences from the introns of the human ob gene, and thereafter to PCR amplify the coding sequence of the ob gene from human genomic DNA so as to identify mutations or allelic variants of the ob gene, all in accordance with protocols described in detail earlier herein.

The current hypothesis is that heterozygous mutations in the ob gene will be associated with mild/moderate obesity while homozygous mutations would be associated with several DNA sequence based diagnostic tests obesity. If this is true, it would allow the ascertainment of people at risk for the development of obesity and make possible the application of drug treatment and/or lifestyle changes before an increased body weight is full developed.

The ob gene may also be useful diagnostically for measurements of its encoded RNA and protein in nutritional disorders. It will be of importance to know, in a particular nutritional disorder, whether ob RNA and/or protein is unregulated or downregulated. Thus, if an obese person has increased levels of ob we would conclude that the problem is downstream of ob, while if ob is reduced we would conclude that inappropriately low levels of ob may be cause of obesity (whether or not the defect is in the ob gene). Conversely, if a cancer or HIV patient who lost weight had elevated levels of ob, we might conclude that inappropriately high expression of ob is responsible for the weight loss.

The cloned human cDNA will be of use for the measurement of the levels of human ob RNA. In addition, recombinant human protein will be prepared and used to develop radioimmunoassays to enable us to measure the fat and perhaps plasma levels of the ob protein.

Agricultural Applications

The ob gene can also be isolated from domestic animals, and the corresponding ob polypeptide obtained thereby. In a specific example, infra, the a probe derived from the murine ob gene hybridizes to corresponding homologous coding sequences from a large number of species of animals. As discussed for human therapies, recombinant proteins can also be prepared and administered to domestic animals. Administration of the polypeptide is desired to produce leaner food animals, such as beef cattle, swine, poultry, sheep, etc. Preferably, an autologous ob polypeptide is administered, although the invention contemplates administration of anti-autologous polypeptide as well. Since the ob polypeptide consists of approximately 160 amino acid residues, it may not be highly immunogenic. Thus, administration of non-autologous polypeptide may not result in an immune response.

Alternatively, the introduction of the cloned genes into transgenic domestic animals would allow one to potentially decrease body weight and adiposity by overexpressing an ob transgene. The simplest means of achieving this would be to target an ob transgene to fat using its own or another fat specific promoter. Increases in body fat might be desirable in other circumstances such as for the development of Kobe beef or fatty liver to make foie gras. This could be accomplished by targeting an antisense ob transgene to fat, or by using gene knockout technology.

Conversely, where an increase in body weight at percentage of fat is desired, an inhibitor or antagonist of the ob polypeptide can be administered. Such inhibitors or antagonists include, but are not limited to, antibodies reactive with the polypeptide, and fragments of the polypeptide that bind but do not activate the ob receptor.

The ob Receptor

Development of small molecule agonists and antagonists of the ob factor will be greatly facilitated by the isolation of its receptor. This can be accomplished by preparing active ob polypeptide and using it to screen an expression library using standard methodology. Receptor binding in the expression library can be tested by administering recombinant polypeptide prepared using either bacterial or mammalian expression vectors, and observing the effects of short term and continuous administration of the recombinant polypeptide on the cells of the expression library, or by directly detecting binding of ob polypeptide to the cells.

As it is presently believed that the ob receptor is likely to be located in the hypothalamus and perhaps liver, preferably cDNA libraries from these tissues will be constructed in standard expression cloning vectors. These cDNA clones would next be introduced into COS cells as pools and the resulting transformants would be screened with active ligand to identify COS cells expressing the ob receptor. Positive clones can then be isolated so as to recover the cloned receptor. The cloned receptor would be used in conjunction with the ob ligand (assuming it is a hormone) to develop the necessary components for screening of small molecule modulators of ob.

Once a recombinant which expresses the ob receptor gene sequence is identified, the recombinant ob receptor can be analyzed. This is achieved by assays based on the physical or functional properties of the ob receptor, including radioactive labelling of the receptor followed by analysis by gel electrophoresis, immunoassay, ligand binding, etc. Furthermore, antibodies to the ob receptor could be generated as described above.

The structure of the ob receptor can be analyzed by various methods known in the art. Preferably, the structure of the various domains, particularly the ob binding site, is analyzed. Structural analysis can be performed by identifying sequence similarity with other known proteins, particular hormone and protein receptors. The degree of similarity (or homology) can provide a basis for predicting structure and function of the ob receptor, or a domain thereof. In a specific embodiment, sequence comparisons can be performed with sequences found in GenBank, using, for example, the FASTA and FASTP programs (Pearson and Lipman, 1988, Proc. Natl. Acad. Sci. USA 85:2444-48).

The protein sequence can be further characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions of the ob receptor protein, which may in turn indicate extracytoplasmic, membrane binding, and intracytoplasmic regions.

Secondary structural analysis (e.g., Chou and Fasman, 1974, Biochemistry 13:222) can also be done, to identify regions of the ob receptor that assume specific secondary structures.

Manipulation, translation, and secondary structure prediction, as well as open reading frame prediction and plotting, can also be accomplished using computer software programs available in the art.

By providing an abundant source of recombinant ob polypeptide, and the opportunity to isolate the ob receptor, the present invention enables quantitative structural determination of the active conformation of the ob polypeptide and the ob receptor, or domains thereof. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967-974; Bar et al., 1985, J. Magn. Reson. 65:355-360; Kimura et al., 1980, Proc. Natl. Acad. Sci. U.S.A. 77:1681-1685). Other methods of structural analysis can also be employed. These include but are not limited to X-ray crystallography (Engstom, A., 1974, Biochem. Exp. Biol. 11:7-13).

More preferably, co-crystals of ob polypeptide and ob receptor can be studied. Analysis of co-crystals provides detailed information about binding, which in turn allows for rational design of ligand agonists and antagonists. Computer modeling can also be used, especially in connection with NMR or X-ray methods (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.).

Identification and isolation of a gene encoding an ob receptor of the invention provides for expression of the receptor in quantities greater than can be isolated from natural sources, or in indicator cells that are specially engineered to indicate the activity of a receptor expressed after transfection or transformation of the cells. According, in addition to rational design of agonists and antagonists based on the structure of ob polypeptide, the present invention contemplates an alternative method for identifying specific ligands of ob receptor using various screening assays known in the art.

Any screening technique known in the art can be used to screen for ob receptor agonists or antagonists. The present invention contemplates screens for small molecule ligands or ligand analogs and mimics, as well as screens for natural ligands that bind to and agonize or antagonize activates ob receptor in vivo.

Knowledge of the primary sequence of the receptor, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, 1990, Science 249:386-390; Cwirla, et al., 1990, Proc. Natl. Acad. Sci., 87:6378-6382; Devlin et al., 1990, Science, 249:404-406), very large libraries can be constructed ($10^6$-$10^8$ chemical entities).

A second approach uses primarily chemical methods, of which the Geysen method (Geysen et al., 1986, Molecular Immunology 23:709-715; Geysen et al. 1987, J. Immunologic Method 102:259-274) and the recent method of Fodor et al. (1991, Science 251, 767-773) are examples. Furka et al. (1988, 14th International Congress of Biochemistry, Volume 5, Abstract FR:013; Furka, 1991, Int. J. Peptide Protein Res. 37:487-493), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., 1993, "Generation and screening of an oligonucleotide encoded synthetic peptide library," Proc. Natl. Acad. Sci. USA 90:10700-4; Lam et al., International Patent Publication No. WO 92/00252, each of which is incorporated herein by reference in its entirety), and the like can be used to screen for ob receptor ligands according to the present invention. With such libraries, receptor antagonists can be detected using cell that express the receptor without actually cloning the ob receptor (Lam et al., supra).

Alternatively, assays for binding of soluble ligand to cells that express recombinant forms of the ob receptor ligand binding domain can be performed. The soluble ligands can be provided readily as recombinant or synthetic ob polypeptide.

The screening can be performed with recombinant cells that express the ob receptor, or alternatively, using purified receptor protein, e.g., produced recombinantly, as described above. For example, the ability of labeled, soluble or solubilized ob receptor that includes the ligand-binding portion of the molecule, to bind ligand can be used to screen libraries, as described in the foregoing references.

EXAMPLE SECTION

The following outlines the method used to identify the genetic material that is exemplary of the present invention. This endeavor comprises four sequential steps; A) Genetic Mapping, B) Physical Mapping, C) Candidate Gene Isolation, and D) Mutation detection. Following confirmation that the murine gene in object was isolated (Step D), the homologous human gene was sought. The steps are summarized in greater detail, below.

A. Genetic Mapping

The mutation was segregated in genetic crosses and standard linkage analysis was used to position the mutation relative to RFLPs (restriction fragment length polymorphisms). These data placed the ob gene in an ~5 cM interval on proximal mouse chromosome 6. (5 cM is a measurement of genetic distance corresponding to 5 apparent genetic crossovers per 100 animals.) A total of 771 informative meioses were generated and used in subsequent genetic mapping (Friedman et al. *Genomics* 11: 1054-1062, 1991). The genetic loci that were mapped relative to ob were all previously published. The two closest RFLPs described were defined by probes derived from the carboxypeptidase and met oncogene genes.

The genetic resolution of the experiments described above was inadequate to clone ob, principally because none of the genetic markers were in tight linkage. In order to identify the requisite tightly linked RFLPs, additional probes were isolated and the genetic cross was expanded. A method known as chromosome microdissection was used to isolate random pieces of DNA from proximal mouse chromosome 6 (Bahary et al., *Mammalian Genome* 4: 511-515, 1993). Individual cloned probes were tested for tight linkage to ob. On the basis of these studies one probe, D6Rck13, also termed psd3, was selected for further analysis owing to its genetic proximity to ob.

This probe was used to genotype the 771 animals described in Bahary et al. as well as 350 animals derived from an additional cross between ob mice and Mus Castaneus mice. On the basis of these data, it was concluded that D6Rck13 was ~0.06 cM distal to ob and was in close enough proximity to ob to begin cloning efforts. D6Rck13 was recombinant to a single animal, #167. An additional probe, Pax-4, was identified that was 0.12 cM proximal to ob. Pax-4 was recombinant in two animals; #111 and 420. Pax-4 is a pseudogene that was previously mapped to proximal mouse chromosome 6 by Gruss and co-workers (Gruss et al. *Genomics* 11:424-434, 1991). On this basis, it was determined that the ob gene resides in the ~0.2 cM interval between Pax-4 and D6Rck13. This led to efforts to clone the interposing DNA in an effort to isolate ob.

B. Physical Mapping

The cloning of the DNA in this interval made use of yeast artificial chromosomes (YACs), a relatively new cloning vector that allows the cloning of long stretches of contiguous DNA often more than 1 million base pairs in length.

Firstly, yeast artificial chromosomes were isolated using D6Rck13 and Pax-4. This was accomplished by preparing purified DNA probes and using them to isolate the corresponding YACs. These YACs (#8, 16, 107 and 24) were isolated and initially characterized, and on the basis of the resulting analyses it was concluded that YAC 16 was the YAC that extended furthest distally, i.e., closest to ob. The key end of YAC #16 was then recovered, and it was determined that this end was closer to ob than Pax-4. This end was termed 16M(+). This conclusion was reached because it was shown that this probe was not recombinant in animal #420 (as was Pax-4). This end clone was sequenced and used to develop a PCR assay. This PCR assay was next used to isolate two new YACs, adu and aad, by screening a YAC library. The crucial YAC for subsequent studies was adu. This YAC was characterized and confirmed to be a non-chimeric 370 kB YAC. The distal end of adu, known as adu (picL) was isolated, and it was determined that adu (+) was non recombinant in all the ob progeny of the genetic crosses including animals #111 and 167.

A PCR assay for this segment was developed using eight specific DNA fragments. Using these primers, 100 kb P1 clones were isolated. P1 phage is a cloning vector that can carry 100,000 base pair genomic inserts. The primers were then used in a PCR screen assay to identify corresponding P1 clones in pools of colonies. Positive pools were then probed for specific clones of interest.

As part of the efforts to complete the physical map of ob, the ends of the D6Rck13 YAC (YAC #53) were isolated. One of the ends, known as 53 Pic1, was used, as well as the key end of YAC aad (known as aad(+)) to isolate additional P1 clones. The ends of these P1 clones were themselves used to isolate new P1 clones. The DNA sequencing of these ends was performed closing a gap between the 53 and aad YACs, and ~2.5 million base pairs of DNA was cloned that spanned Pax-4, 16M(+), adu (+), aad(Pic1), 53 (Pic1) and D6Rck13. An ~500 kB subset of this region was isolated in P1 clones. By carefully mapping the sites of recombination apparent in animals 111 and 167, it was concluded that ob was situated in an ~400,000 base pair interval that was spanned by a contiguous series of P1 clones. The key P1 clones, 322 and 323, were among those selected for further analyses.

The physical map of the portion of the chromosome carrying ob is shown in FIG. 7A. FIG. 7B represents the YAC cloning vectors that contain ob, or regions proximal to the gene.

C. Isolation of Candidate Genes

The method used to isolate genes in this interval was exon trapping (FIG. 7C). This method used a vector (available from Gibco-BRL Life Sciences) to identify exon DNA (i.e., coding sequences) by selecting for functional splice acceptor and donor sequences in genomic DNA introduced into a test construct. Initial attempts at exon trapping were performed using cosmid subclones derived from YAC #53. These initial efforts were unsuccessful. Subsequently, these studies were initiated using a subset of the P1 clones: 322, 323, 324, 325, and 259. The DNA from these P1s were grown and subcloned into the exon trapping vector. The experiment was repeated using various P1 clones. In these and one subsequent exon trapping experiment, three candidate genes for ob were identified: 325-2, 323-8 and a previously cloned gene, Inosine Monophosphate Dehydrogenase (IMPDH). The IMPDH gene had been previously cloned but had not been mapped, and its proximity to ob was previously unknown. 325-2 was subsequently shown to be a testis specific gene, while 323-8 was shown to encode a rare brain transcript. None of these genes appeared to encode ob.

After three unsuccessful efforts to exon trap the ob gene, another attempt was made by preparing DNA from all the P1s from the critical ob region. These included P1s: 258, 259, 322, 323, 324, 325, 498, 499, 500, 653, 654 and numerous others.

Thereafter P1s 258, 260, 322, 498 and 499 were subcloned into the exon trapping vector, and subsequently several plates were prepared with bacterial clones, each of which carried a putative exon. Approximately 192 clones representing putative ob candidates were obtained. These clones were short inserts cloned into the pGem vector.

Figure 8:
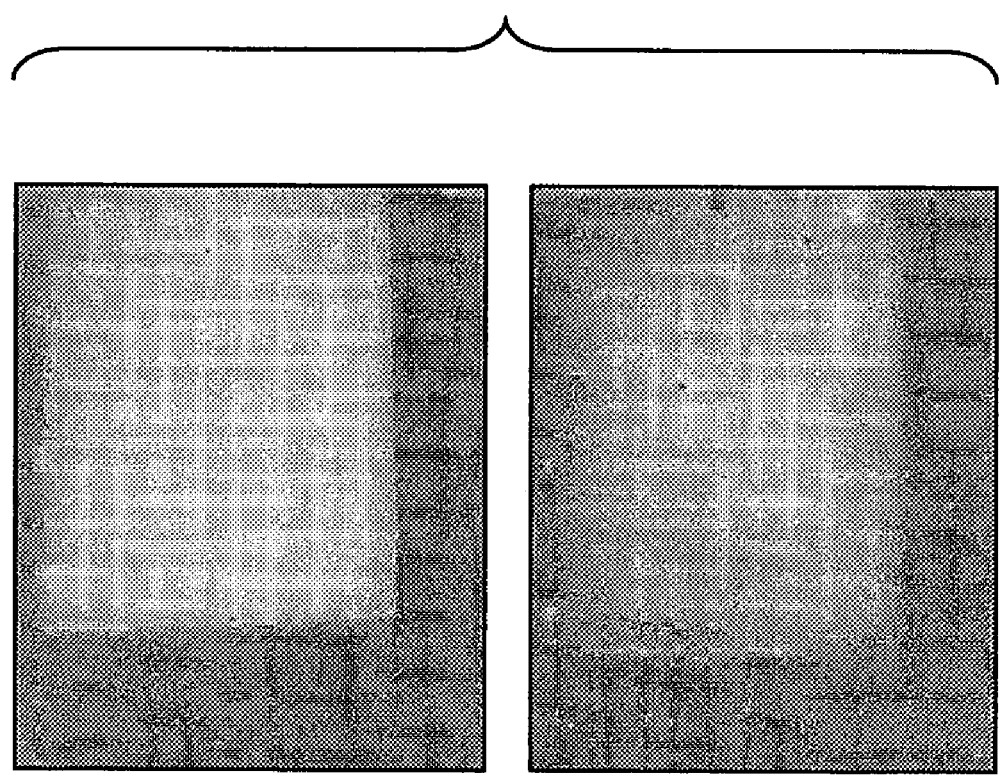
FIG. 8 present a photograph of an ethidium bromide stain of 192 independent isolates of the exon trapping experiment that were characterized.
Figure 9:
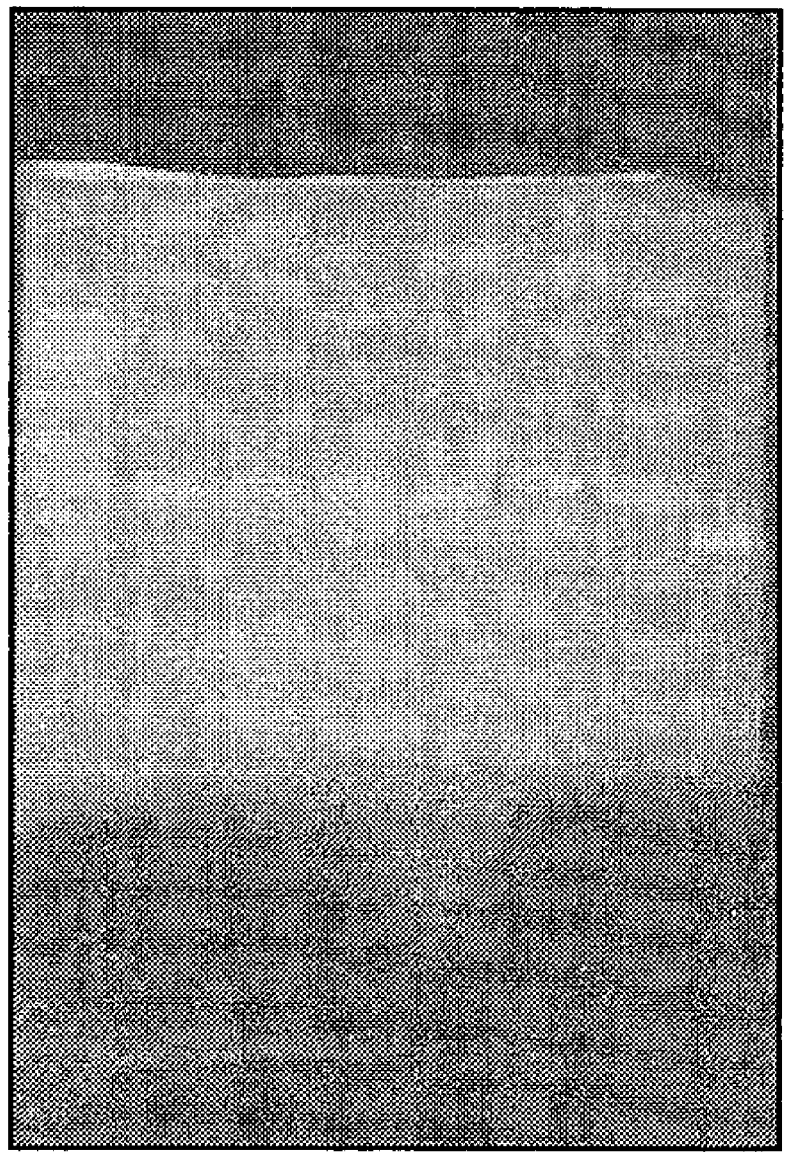
FIG. 9 is a photograph of an ethidium bromide stain of PCR-amplified clones suspected of carrying ob. Each of the 7 clones that did not carry the artifact was reamplified using PCR and electrophoresed on a 1% agarose gel in TBE and stained with ethidium bromide. The size markers (far left unnumbered lane) are the commercially available "1 kB ladder". Lane 1—clone 1D12, containing an "HIV sequence." Lane 2—clone 1F1, a novel clone outside of the ob region. Lane 3—clone 1H3. Lane 4—clone 2B2, which is the identical to 1F1. Lane 5—clone 2G7, which contains an ob exon. Lane 6—clone 2G11, which is identical to 1F1. Lane 7—clone 2H1, which does not contain an insert.

Each clone was PCR amplified with PCR primers corresponding to plasmid sequences that flanked the insert. The PCR amplification was performed directly on the bacteria that carried the plasmid. The reactions were set up using a Biomek robot. The PCR products were electrophoresed on a 1% agarose gel in TBE buffer that contained ethidium bromide (FIG. 8). Based on our previous experience, we found a consistent artifact such that many of the isolates contained two trapped exons derived from the vector. We identified the clones both by their size and the fact that hybridization of DNA probes corresponding to this artifact lot hybridized to the corresponding bands on a Southern blot of this gel (data not shown). In this way we excluded 185 of the clones from further evaluation.

Thus, the 192 exons, a total of seven exons were selected for further study. The templates for sequencing were prepared and sequencing was performed. The results are presented in FIG. 7. The sequences for the 7 exons were analyzed and it was found that 4 were identical and one was an apparent artifact. In particular, clone 1D12 contained the "HIV sequence", which refers to the so called artifact band. The exon trapping vector includes HIV sequences; a short segment of these vector sequences corresponds to this artifact. This left three exons for further analysis: 1F1, 2G7 and 1H3. 1F1 was eliminated because it mapped outside the critical region.

PCR primers for 2G7 were selected and synthesized. The primers used were:

```
                            (SEQ ID NO: 7)
5' CCA GGG CAG GAA AAT GTG   (Tm = 60.0)

(SEQ ID NO: 8)
3' CAT CCT GGA CTT TCT GGA TAG G  (Tm = 60.0)
```

These primers amplified genome DNA with PCR conditions as follows: 25-30 cycles with 55° annealing×2', 72° extension×2', 94' denaturation×1' in standard PCR buffer. These primers were also used to generate a labeled probe by including $^{32}$P dCTP in the PCR reaction with a corresponding reduction in the amount of cold dCTP. The sequence of the exon on 2G7 was determined, and is shown in FIG. 10 (SEQ ID NO:9). The portions of the sequence corresponding to the PCR primers are underlined.

Figure 11:
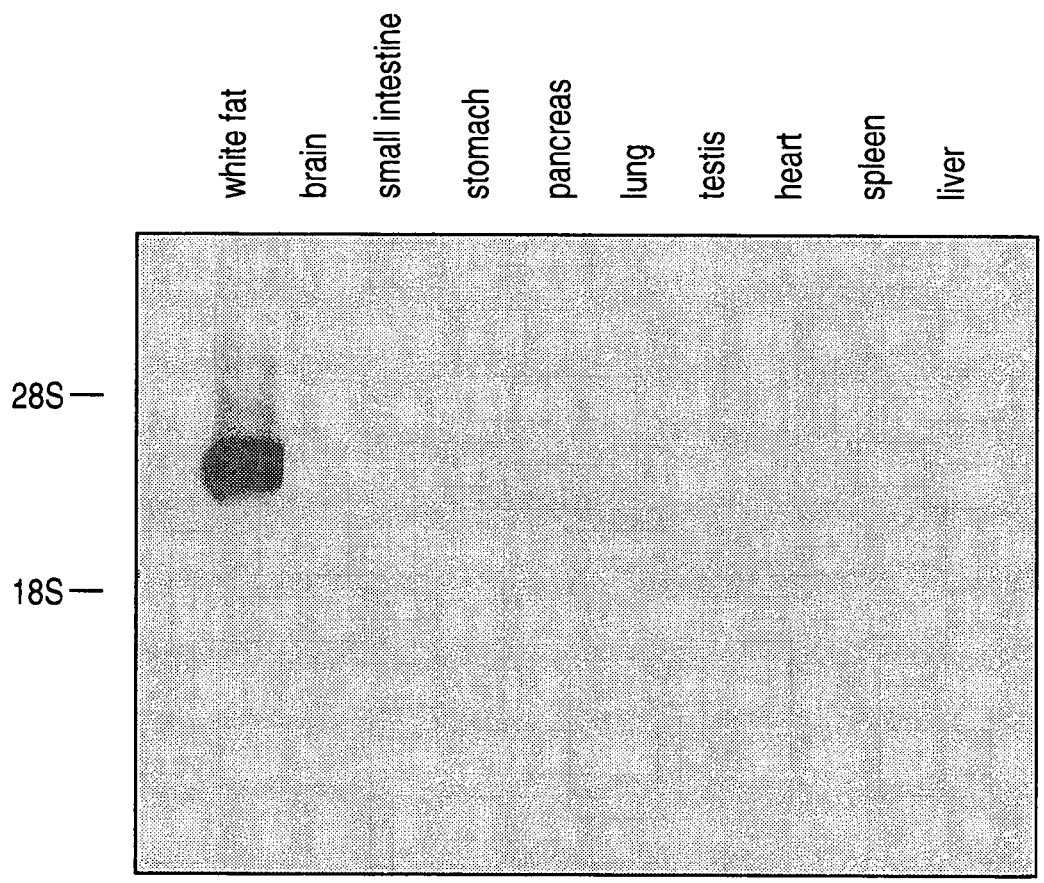
FIG. 11 is a Northern blot of mRNA from different organs of the mouse using PCR labeled 2G7 as a probe. Ten μg of total RNA from each of the tissues was electrophoresed on an agarose gel with formaldehyde. The probe was hybridized at 65° C. in Rapid Hybe (Amersham).

An RT PCR was performed on a variety of tissue RNAs and it was concluded that 2G7 was expressed exclusively in fat (not shown). Thereafter, $^{32}$P-labelled 2G7 was hybridized to a Northern blot of tissue RNAs (FIG. 11) and showed that its RNA was expressed at high level in fat tissue but was either not expressed or expressed at very low levels in all other tissues (where the signals may be the result of fat contaminating the tissue preparations). Ten µg of total RNA from each of the tissues listed was electrophoresed on an agarose gel with formaldehyde. The probe was hybridized at 65° in a standard hybridization buffer, Rapid Hype (Amersham).

The size of the RNA was ~4.9 kB. At this point 2G7 was considered to be a viable candidate gene for ob and was analyzed further.

D. Mutation Detection

Figure 12:
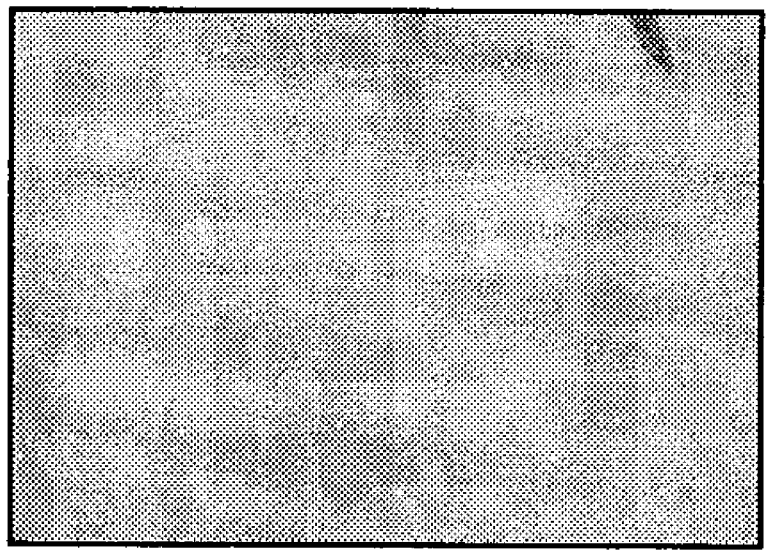
FIG. 12 is an ethidium bromide stain from an RT PCR reaction on fat cell RNA from each of the mouse strains listed. Total RNA for each sample was reverse transcribed using oligo dT and reverse transcriptase, and the resulting single stranded cDNA was PCR amplified with the 2G7 primers (lower bands) or actin primers (upper bands). The products were run on a 1% agarose TBE gel.

In order to confirm that 2G7 encoded the ob gene, it was necessary to demonstrate differences in the levels of RNA expression of DNA sequence of this gene in mutant as compared to wild type animals. Two separate mutations of the ob gene are available for study, C57BL/6J ob/ob (1J) and Ckc/Smj ob/ob (2J). These will be referred hereinafter as 1J and 2J, respectively. (Informal nomenclature is used to refer to the mouse strains studied. Throughout this specification and in the drawings, it will be understood that C57BL/6J refers to C57BL/6J +/+; CKC/smj refers to SM/Ckc-+$^{Dac}$-+/+; CKC/smj ob/ob refers to SM/Ckc-+$^{Dac}$-ob$^{2J}$/ob$^{2J}$.) RNA was prepared from fat tissue that had been isolated from 1J, 2J, and control animals. Total RNA for each sample was reverse transcribed using oligo dT and reverse transcriptase. The resulting single stranded cDNA was then PCR amplified either with the 2G7 primers (conditions shown above) for the lower band or commercially available actin primers for the upper band. The RT PCR products were run on a 1% agarose TBE gel that was stained with ethidium bromide (FIG. 12). Using RT PCR it was found that 2G7 mRNA was absent in 2J mice. 2G7 mRNA was absent, when tested by RT PCR, from four additional 2J animals.

Figure 13:
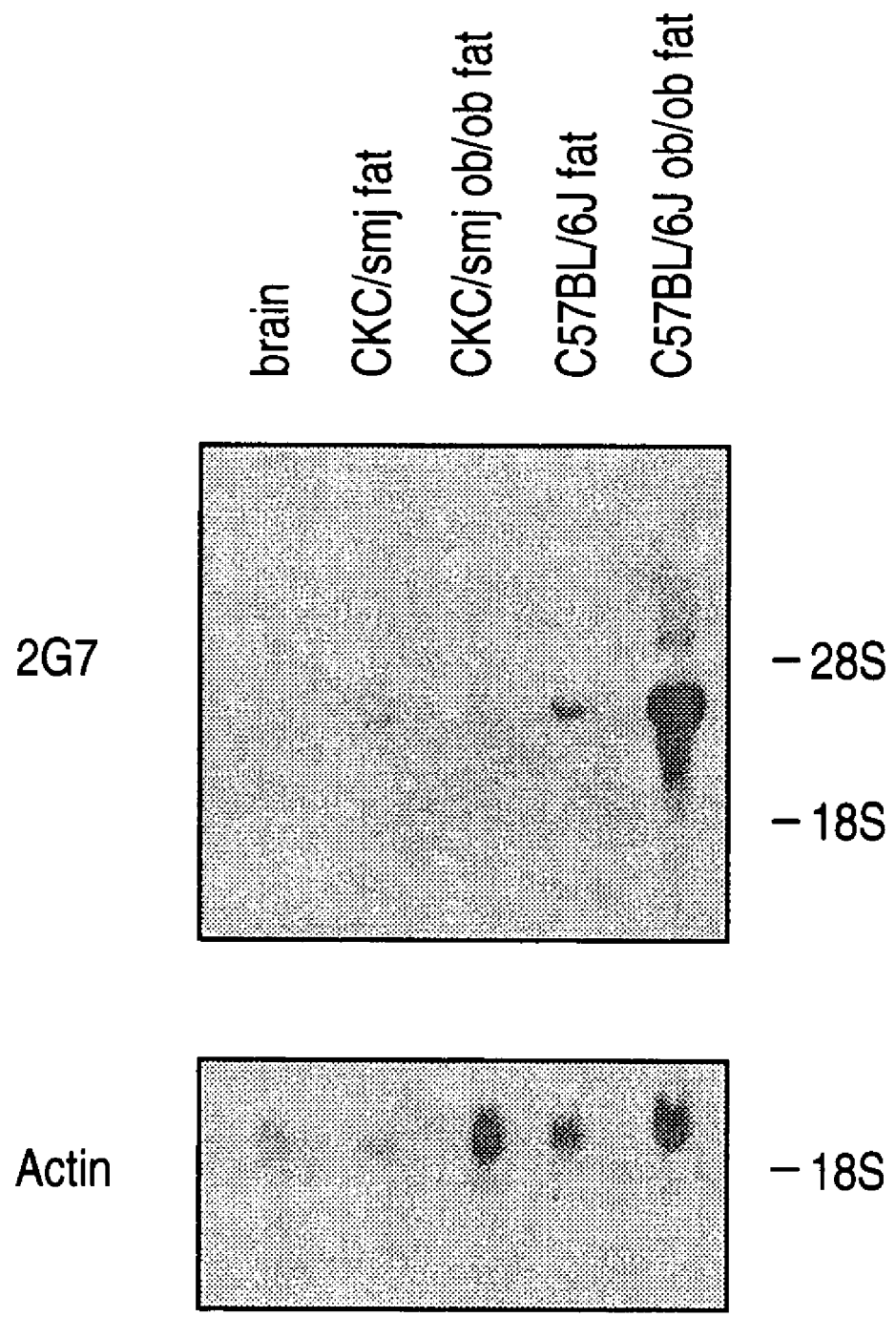
FIG. 13 is a Northern analysis corresponding to the data in FIG. 12. Ten μg of fat cell RNA were run out and probed with the PCR labeled 2G7 probe as in FIG. 11, above.

This result was confirmed on a Northern blot (FIG. 13). Ten µg of fat cell RNA from each of the strains were run out. The blot was probed with the 2G7 probe that was PCR labeled, as discussed. Actin is a control for the amount of RNA loaded. This probe was labeled by PCR amplification of the material, i.e., band, in FIG. 11 using $^{32}$P-dCTP in the PCR reaction. The actin signal is fairly similar in all of the samples. The ob signal is absent in brain because the mRNA is specific to fat cells.

The results of the Northern analysis confirm that 2G7 RNA was absent in 2J mice. The ob RNA is absent in the CKC/smj ob/ob mice because in this obese mutant strain the gene is disrupted such that no RNA is made. In addition, the level of 2G7 RNA was increased ~10-20 fold in 1J as well as db/db fat. These results are compatible with the hypothesis that ob either encodes circulating hormone or is responsible for the generation of a signal from fat cells that modulate body weight. At this point it was concluded that 2G7 is the ob gene and predicted that 1J mice have a point mutation, probably a nonsense mutation leading to a premature translation termination.

These Northern results have been replicated using fat cell RNA preparations from four different 2J animals (FIG. 14). In this assay, ap2 is a fat-specific transcript that was used as a control much the same as actin in FIG. 13. There is no significance to the varying density of the ap2 band. ap2 was labeled by designing PCR primers form the published ap2 sequence. The RT PCR products of fat cell RNA were then relabeled using the same protocol for PCR labeling. This analysis demonstrates the presence of ob mRNA in normal homozygous or heterozygous animals, and its absence from 2J mutant animals.

Using the labeled 2G7 PCR probe, a total of 50 mouse cDNA clones from a murine fat cell λgt11 cDNA library (Clonetech 5'-STRETCH cDNA from testicular fat pads of Swiss mice, #ML3005b), and thirty cross hybridizing human cDNA clones from a human fat cell λgt10 cDNA library (Clonetech 5'-STRETCH cDNA from abdomen #HL1108a) were isolated. Library screening was performed using the plaque lift procedure. The filters from the plaque lift were denatured using the autoclave method. The filters were hybridized in duplicate with the PCR labeled 2G7 probe (Rapid Hybe buffer, 65° C., overnight). After a 2-4 hour prehybridization, the filters were washed in 2×SSC, 2% SDS, twice for 30 minutes at 65° C. and exposed to SRy Llim. Duplicate positives were plaque purified. Plaque purified phage were PCR amplified using commercially available vector primers. For example, λgt10 and λgt11. The resulting PCR products corresponded to the cDNA insert for each phage with a small amount of vector sequence at either end. The bands were gel purified and sequenced using the ABI automated sequencer and the vector primers to probe the DNA polymerase. Additional sequence information was generated within each clone by synthesizing internal primers derived from the DNA sequence and repeating the DNA sequence reaction.

Sequencing of the coding sequence of these clones is complete (see FIGS. 1 and 3, SEQ ID NOS:1 and 2). Sequencing of the adjacent regions is continuing, and to date, ~1600 bp of sequence from five prime end of the murine mRNA has been compiled. The sequence data suggest that the ob gene encodes a 160 amino acid protein that has the features of a secreted protein. In addition, the sequence of the homologous human gene is complete (FIGS. 2 and 4, SEQ ID NOS:3 and 4), and extensive homology between the mouse and human genes has been demonstrated.

Figure 15:
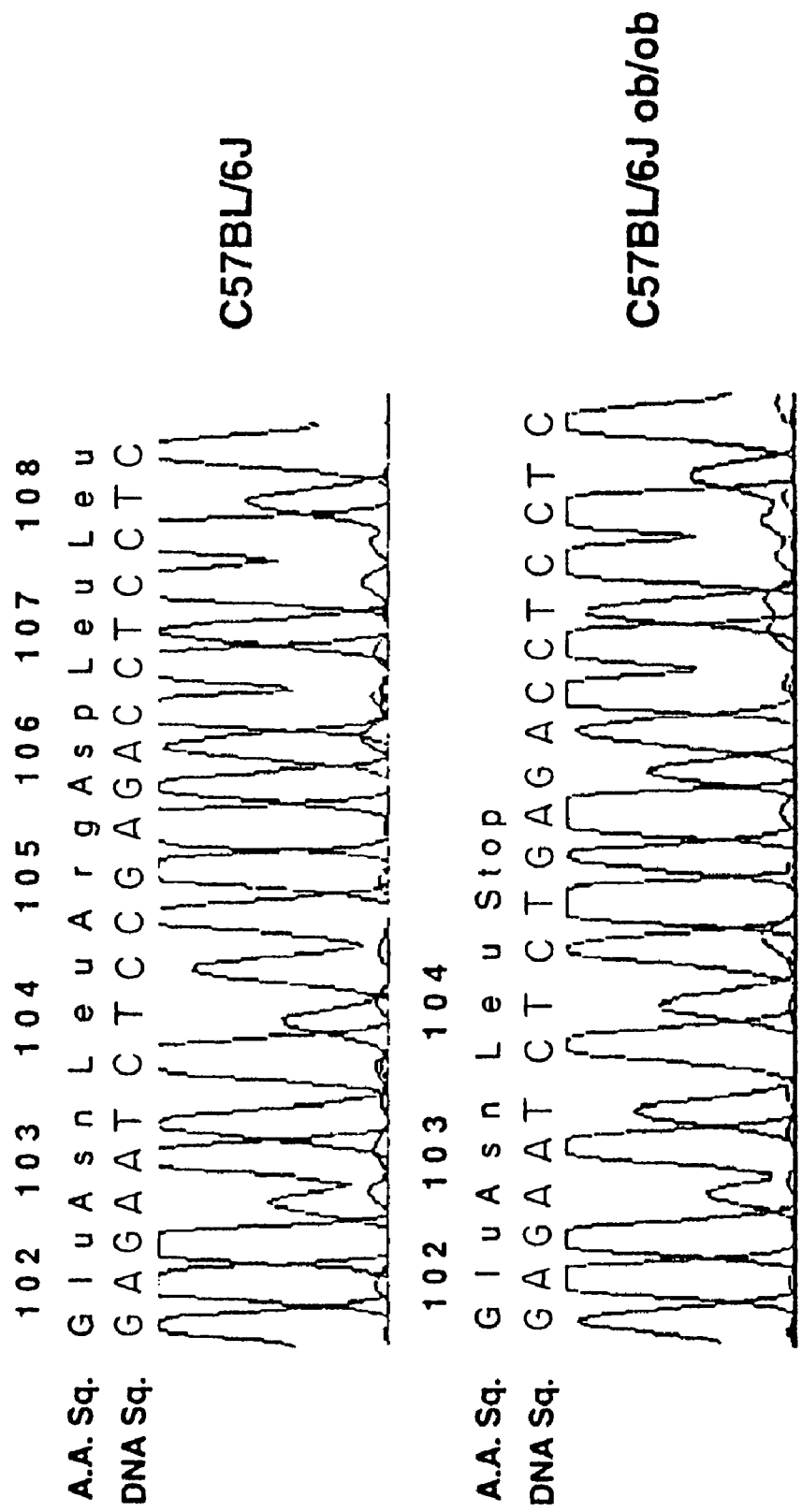
FIG. 15 compares the DNA sequence of the C57BL/6J and the ob 1J mice. The chromatogram shown is the output of a DNA sequencing reaction using an Applied Biosystem 373A automated DNA sequencer.

The mutation has been identified in 1J mice. The mutation is G-A base change that results in an apparent premature stop codon at amino acid 108 and in all likelihood accounts for the 1J mutation (FIG. 15) despite expression of the ob mRNA (see FIGS. 12 and 13, C57BL/6J ob/ob lanes).

More recently, Southern blots have been used to conclude that the 2J mutation is the result of a detectable DNA change at the 5' end of ob that appears to completely abolish RNA expression. The exact nature of this possible rearrangement remains to be determined.

Figure 16:
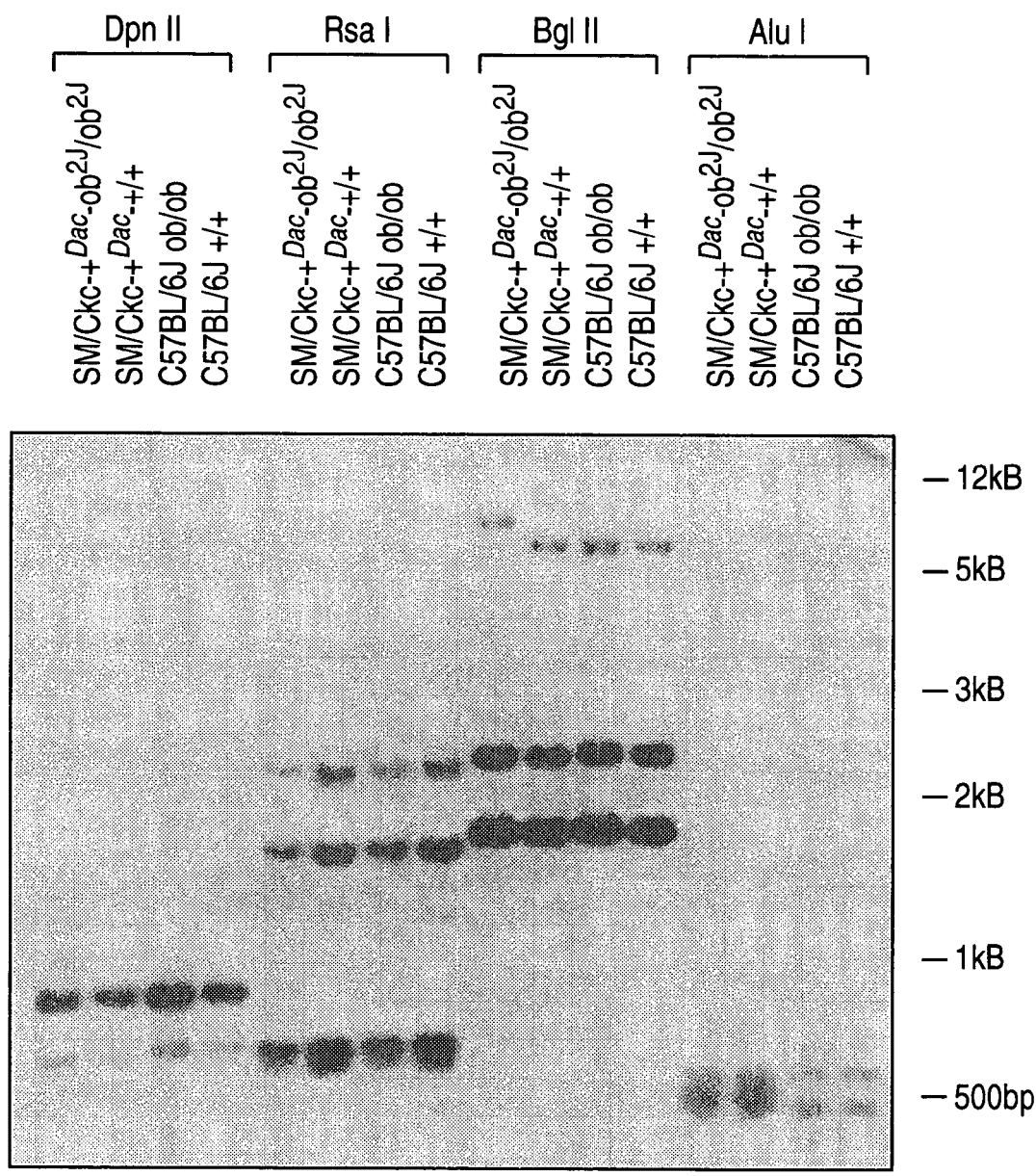
FIG. 16 is a genomic southern blot of genomic DNA from each of the mouse strains listed. Approximately 10 μg of DNA (derived from genomic DNA prepared from liver, kidney or spleen) was restriction digested with the restriction enzyme indicated. The DNA was then electrophoresed in a 1% agarose TBE gel and probed with PCR labeled 2G7.

A genomic Southern blot of DNA from the CKC/smj (SM/Ckc-+$^{Dac}$) and C57BL/6J mice using four different restriction endonucleases was performed in order to determine whether the mutant ob yielded a unique fragment pattern (FIG. 16). Approximately 10 µg of DNA (derived from genomic DNA prepared from liver, kidney, or spleen) was restriction digested with the restriction enzyme indicated. The DNA was then electrophoresed in a 1% agarose TBE gel. The DNA was transferred to an imobilon membrane and hybridized to the PCR labeled 2G7 probe. The key band is the uppermost band in the BglII digest for the CKC/smj ob/ob (SM/Ckc-+$^{DAC}$ ob$^{2J}$/ob$^{2J}$) DNA. This band is of higher molecular weight than in the other strain, indicating a mutation in this strain.

Figure 17:
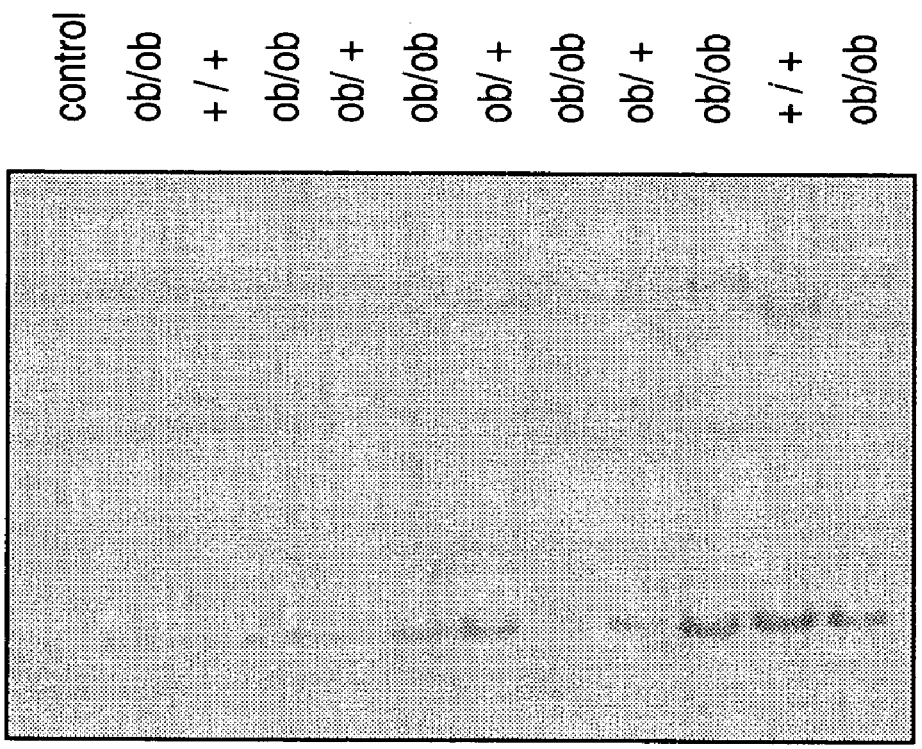
FIG. 17 is a Southern blot of BglII digests of genomic DNA from the progeny of an $ob^{2J}/+$ $ob^{2J}/+$ cross.

FIG. 17 is a southern blot of a BglII digest of genomic DNA from the progeny of an ob$^{2J}$/+×ob$^{2J}$/+ cross. Some of the DNAs have only the upper band, some only the lower band, and some have the both bands. The animals with only the upper band are allo-obese, i.e., ob$^{2J}$/ob$^{2J}$. These data show that the polymorphism (i.e., mutation) shown in FIG. 16 segregates in a genetic sense.

Figure 18:
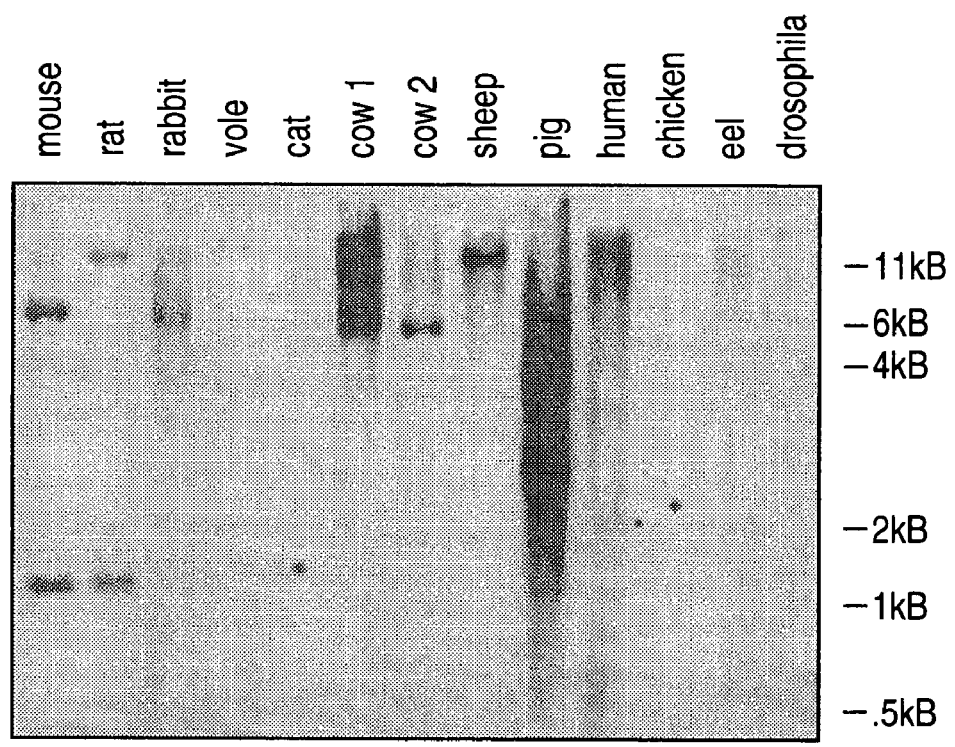
FIG. 18 is a Southern blot of EcoRI digested DNA from the species listed, using 2G7 as a probe. The restricted DNA was run on a 1% agarose TBE gel, and transferred to an imobilon membrane for probing. The filter was hybridized at 65° C. in Rapid Hype buffer, and washed with 2×SSC, 2% SDS at 65° C. twice for 30 minutes each.

Genomic DNA was isolated from mouse, rat, rabbit vole, cat, cow, sheep, pig, human, chicken, eel, and *drosophila*, and restriction digested with EcoR1. The digests were electrophoresed on 1% agarose TBE gel. DNA was transferred to an immobilon membrane and probed with the PCR labeled 2G7 probe. The filter was hybridized at 65° C. in Rapid Hype Buffer and washed with 2×SSC, 2% SDS at 65° C. twice for 30 minutes each wash, i.e., there were two buffer changes. These data indicate that ob is conserved among vertebrates (FIG. 18). Note in this regard that there is a 2 (+) signal in eel DNA; eel is a fish.

In summary, available evidence suggests that body weight and adiposity are physiologically controlled. Seven years ago efforts began to identify two of the key components of this system: the ob and db genes. As shown in this example, the ob gene has now been identified as a fat specific gene that plays a key role in regulating body weight. The product of this gene, which is most probably a secreted hormone, will have important implications for the diagnosis and treatment of nutritional disorders in man and non-human animals.

Example

Identification of a Putative Signal Sequence

The putative signal sequence of the full length murine ob gene was determined by application of a computer algorithm to the method of von Heijne (*Nucl. Acids Res.* 14, 4683, 1986). Using this technique, the most probable signal sequence was identified in the polypeptide coding region corresponding to amino acids 9-23, having the sequence:

FLWLWSYLSYVQA ↑ VP (SEQ ID NO:10)

in which the arrow indicates the putative signal sequence cleavage site.

Example

Expression of ob In Bacteria

Both murine and human cDNAs encoding ob have been cloned into a pET-15b expression vector (Novagen). This vector contains a T7 promoter in conjunction with a lac operator, and expresses a fusion protein containing a histidine tag (His-Tag) and a thrombin cleavage site immediately upstream of the coding sequence insertion site (FIG. 19) (SEQ ID No:11).

The mouse and human cDNAs were modified such that the alanine at the end of the signal sequence was turned into an NdeI site, as was a separate sequence in the 3' region. Insertion of the NdeI site was accomplished using PCR with novel primers:

```
Mnde 5' (murine five prime primer):(SEQ ID NO: 12)
CTTATGTTCA TATGGTGCCG ATCCAGAAAG TC Mnde-3'
(murine three prime primer):       (SEQ ID NO: 13)
TCCCTCTACA TATGTCTTGG GAGCCTGGTG GC Hnde-5' (human five prime primer): (SEQ ID NO: 14)
TCTATGTCCA TATGGTGCCG ATCCAAAAAG TC Hnde-3' (human three prime primer):(SEQ ID NO: 15)
TTCCTTCCCA TATGGTACTC CTTGCAGGAA GA
```

The primers contain a 6-base pair mismatch in the middle that introduces NdeI restriction sites at each end of the PCR fragment. Phage carrying either the mouse or human cDNA were PCR amplified using those primers. The PCR product was digested with NdeI and gel purified on a 1% low melting point agarose gel. The gel purified bands were subcloned into the pET vector. The resulting plasmids were sequenced to ensure that mutations were not introduced during the PCR amplification step of cloning. To date constructs for the human and mouse cDNA with glutamine have been prepared; similar constructs are now being made using the same primers and methods to introduce the coding sequence without the glutamine (see the next Example).

Example

Both Murine and Human ob Genes Are Found in Two Isoforms

An unexpected deletion was observed in about one out of three cDNA clones of the human and murine ob gene. In particular, a three base-pair deletion, corresponding to the glutamine 49 codon, resulted in a deduced amino acid sequence lacking a glutamine residue at position 49 of the full length murine (FIG. 5; SEQ ID NO:5) and human (FIG. 6; SEQ ID NO:6) polypeptides. This deletion corresponds to nucleotides 260-261-262 from the murine cDNA sequence (FIG. 1; SEQ ID NO:1), and to nucleotides 182-183-184 on the human sequence (FIG. 2; SEQ ID NO:3).

The missing codon for glutamine 49 in the cDNA sequences immediately follows the 2G7 exon. The sequence of 2G7 corresponds to the sequence immediately upstream of the codon for gln-49 in the mouse ob gene (compare FIG. 10 with FIG. 1). We postulate that some of the cDNA lack the gln-49 CAG codon because this is at a splice acceptor site. Since AG is the actual acceptor site, slippage of the machinery in some cases would lead to deletion of the CAG codon. This is shown below:

```
        gln ser val
    ag  CAG TCG GTA  (with glutamine)      (SEQ ID NO: 16)
        ↑
(splice acceptor site)

ser val
    ag  CAG TCG GTA  (without glutamine)   (SEQ ID NO: 17)
        ↑
    (splice acceptor site)
```

The "ag" in the sequences above corresponds to the assumed intron sequence upstream of the glutamine codon, and AG is the putative alternative splice site.

Example

Preparation of Antibodies to the ob Polypeptide

A set of four peptide sequences from the deduced murine ob sequence were identified using immunogenicity plot software (GCG Package). The four carboxyl terminal peptide fragments are:

```
Val-Pro-Ile-Gln-Lys-Val-Gln-Asp-      (SEQ ID NO: 18)
Asp-Thr-Lys-Thr-Leu-Ile-Lys-Thr:

Leu-His-Pro-Ile-Leu-Ser-Leu-Ser-      (SEQ ID NO: 19)
Lys-Met-Asp-Gln-Thr-Leu-Ala:

Ser-Lys-Ser-Cys-Ser-Leu-Pro-Gln-      (SEQ ID NO: 20)
Thr-Ser-Gly-Leu-Gln-Lys-Pro-Glu-
Ser-Leu-Asp:

Ser-Arg-Leu-Gln-Gly-Ser-Leu-Gln-      (SEQ ID NO: 21)
Asp-Ile-Leu-Gln-Gln-Leu-Asp-Val-
Ser-Pro-Glu-Cys:
```

These peptides were conjugated to KLH, and the peptide-KLH conjugates were used to immunize rabbits using standard techniques. Polyclonal antisera specific for each peptide is recovered from the rabbits.

The following is a list of references related to the above disclosure and particularly to the experimental procedures and discussions.

Bahary, N.; G. Zorich; J. D. Pachter; R. L. Leibel; and J. M. Friedman. 1991. Molecular genetic linkage maps of mouse chromosomes 4 and 6. *Genomics* 11:33-47.

Bahary, N.; D. McGraw; R. L. Leibel; and J. M. Friedman. 1991. Chromosomal microdissection of midmouse chromosome 4: Mapping of microclones relative to the mouse db gene. Submitted.

Bahary, N.; J. Pachter; R. Felman; R. L. Leibel; K. A. Albright; S. Cram; and J. M. Friedman. 1991. Molecular mapping of mouse chromosomes 4 and 6: Use of a flow-sorted Robertsonian chromosome. Submitted.

Blank, R.; J. Eppig; F. T. Fiedorek; W. N. Frankel; J. M. Friedman; K. Huppi; I. Jackson; and B. Mock. 1991. Mouse chromosome 4. *Mammalian Genome* 1(suppl): s51-s78.

Bogardus, C.; Ravussin, E.; Abbot, W.; Zasakzku, J. K.; Young, A.; Knowler, W. C.; Friedman, J. M.; R. L. Leibel; N. Bahary; D. A. Siegel; and G. Truett, G. 1991. Genetic analysis of complex disorders: Molecular mapping of obesity genes in mice and humans *Annals of the New York Academy of Sciences* 630:100-115.

Friedman, J. M.; R. L. Leibel; and N. Bahary. 1991. Molecular mapping of obesity genes. Mammalian Genome 1:130-144.

Friedman, J. M.; R. L. Leibel; N. Bahary; and G. Zorich. 1991. Molecular mapping of the mouse ob mutation. *Genomics*, (in press).

Harris, M. I. (1991). Diabetes Care 14 (suppl. 3), 639-648.

Harris, M. I.; Hadden, W. C.; Knowler, W. C.; and Bennett, P. H. (1987). Diabetes 36, 523-534.

Harris, R. B. S. (1990). FASEB J. 4, 3310-3318.

Jacobowitz, R., and Moll, P. O. (1986). N. Engl. J. Med. 315, 96-100

Kessey, R. E. (1980). In Obesity, A. Stunkard, eds. (Philadelphia: W. B. Sauders Co.), pp. 144-166.

Kessey, R. E., and Pawley, T. L. (1986). Annu. Rev. Psychol. 37, 109-133.22

Leibel, R. L., N. Bahary and J. M. Friedman. 1990. Genetic variation and nutrition in obesity: Approaches to the molecular genetics of obesity. In *Genetic variation and Nutrition* (Simopoulos, A. P. and Childs, B., eds.), S. Karger, Basel, pp. 90-101.

Siegel, D.; N. G. Irving; J. M. Friedman; and B. J. Wainwright. 1991. Localization of the cystic fibrosis transmembrane conductance regulator to mouse chromosome 6. *Cytogenetics Cell Genetics*, submitted.

Truett, G. E.; N. Bahary; J. M. Friedman; and R. L. Leibel. 1991. The rat obesity fatty (fa) maps to chromosome 5:Evidence for homology with the mouse gene diabetes (db). *Proc. Natl. Acad. Sci. USA* 88:7806-7809.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

Various references are cited throughout this specification, each of which is incorporated herein by reference in its entirety.

What is claimed is:

1. A method for measuring the presence of an ob polypeptide, an immunogenic fragment thereof, an immunogenic derivative thereof, or an immunogenic analog thereof, in a sample, comprising:
   A. contacting a sample suspected of containing an ob polypeptide, an immunogenic fragment thereof, an immunogenic derivative thereof, or an immunogenic analog thereof, with an antibody that binds to an epitope of said ob polypeptide, immunogenic fragment thereof, immunogenic derivative thereof, or immunogenic analog thereof, said epitope having an amino acid sequence set out in SEQ ID NO:2, SEQ ID NO:4, SEQ ID NO:5, or SEQ ID NO:6, under conditions which allow for the formation of reaction complexes comprising the antibody and said ob polypeptide, immunogenic fragment thereof, immunogenic derivative thereof, or immunogenic analog thereof; and
   B. detecting the formation of said reaction complexes in the sample; in which detection of the formation of reaction complexes indicates the presence of said ob polypeptide, immunogenic fragment thereof, immunogenic derivative thereof, or immunogenic analog thereof in said sample.

2. The method of claim 1 in which the antibody is bound to a solid phase support.

3. The method of claim 2 which further comprises contacting the sample with a labelled ob polypeptide step (A), and removing unbound substances prior to step (B), and in which the formation of reaction complexes in the sample is detected by observing a decrease in the amount of labelled ob polypeptide in the sample.

4. The method of claim 2 which further comprises contacting the sample with a labelled antibody in step (A), which labelled antibody is an anti-ob polypeptide antibody, and removing unbound substances prior to step (B), and in which the formation of reaction complexes in the sample is detected by observing an increase in the amount of labelled antibody in the sample.

5. The method of claim 1 in which an ob polypeptide is bound to a solid phase support.

6. The method of claim 5 which further comprises contacting the sample with an ob polypeptide in step (A), and removing unbound substances prior to step (B), and in which the antibody is labelled and the formation of reaction complexes in the sample is detected by observing a decrease in the amount of labelled antibody.

7. A method for evaluating the level of ob polypeptide in a biological sample comprising
   A. detecting the formation of reaction complexes in a biological sample according to the method of claim 1;
   B. determining the amount of reaction complexes formed, which amount of reaction complexes corresponds to the level of ob polypeptide in the biological sample; and
   C. comparing the amount determined in step B. with an amount of ob polypeptide in a control sample in order to evaluate the level of ob polypeptide in the biological sample.

8. A method for detecting or diagnosing the presence of a disease associated with elevated or decreased levels of ob polypeptide in a mammalian subject comprising:
   A. evaluating the level of ob polypeptide in a biological sample from a mammalian subject according to claim 7; and
   B. comparing the level detected in step (A) to a level of ob polypeptide present in normals or in the subject at an earlier time;
   in which an increase in the level of ob polypeptide as compared to normal levels indicates a disease associated with elevated levels of ob polypeptide, and decreased level of ob polypeptide as compared to normal levels indicates a disease associated with decreased levels of ob polypeptide.

9. A method for monitoring a therapeutic treatment of a disease associated with elevated or decreased levels of ob polypeptide in a mammalian subject comprising evaluating the levels of ob polypeptide in a series of biological samples obtained at different time points from a mammalian subject undergoing a therapeutic treatment for a disease associated with elevated or decreased levels of ob polypeptide according to the method of claim 7.

10. The method according to claim 8 or 9, wherein the disease associated with elevated levels of ob polypeptide is selected from the group consisting of AIDS, cachexia, cancer, and anorexia nervosa.

11. The method according to claim 8 or 9, wherein the disease associated with decreased levels of ob polypeptide is selected from the group consisting of obesity, Type II diabetes, hypertension, and elevated blood lipids.

* * * * *

UNITED STATES PATENT AND TRADEMARK OFFICE
CERTIFICATE OF CORRECTION

PATENT NO. : 7,521,258 B2
APPLICATION NO. : 10/780295
DATED : April 21, 2009
INVENTOR(S) : Friedman et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

Signed and Sealed this
Twenty-third Day of August, 2011

David J. Kappos
*Director of the United States Patent and Trademark Office*

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 701 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (vi) ORIGINAL SOURCE:
      (A) ORGANISM: Mus musculus (xi) SEQUENCE DESCRIPTION: SEQ ID NO: 1:

```
CCAGCAGCTG CAAGGTGCAA GAAGAAGAAG ATCCCAGGGA GGAAAATGTG CTGGAGACCC    60
CTGTGTCGGN TTCCTGTGGC TTTGGTCCTA TCTGTCTTAT GTTCAAGCAG TGCCTATCCA   120
GAAAGTCCAG GATGACACCA AAACCCTCAT CAAGACCATT GTCACCAGGA TCAATGACAT   180
TTCACACACG CAGTCGGTAT CCGCCAAGCA GAGGGTCACT GGCTTGGACT TCATTCCTGG   240
GCTTCACCCC ATTCTGAGTT GTTCCAAGAT GGACCAGACT CTGGCAGTCT ATCAACAGGT   300
CCTCACCAGC CTGCCTTCCC AAAATGTGCT GCAGATAGCC AATGACCTGG AGAATCTCCG   360
AGACCTCCTC CATCTGCTGG CCTTCTCCAA GAGCTGCTCC CTGCCTCAGA CCAGTGGCCT   420
GCAGAAGCCA GAGAGCCTGG ATGGCGTCCT GGAAGCCTCA CTCTACTCCA CAGAGGTGGT   480
GGCTTTGAGC AGGCTGCAGG GCTCTCTGCA GGACATTCTT CAACAGTTGG ATGTTAGCCC   540
TGAATGCTGA AGTTTCAAAG GCCACNCAGG CTCCCAAGAA TCATGTAGAG GGAAGAAACC   600
TTGGCTTCCA GGGGTCTTCA GGANNGAAGA GNAGCNCATG TGCACACNNN ATCCANNNNT   660
CATTCANTTT CTCTCCCTCC TGTAGACCAC NNNNCCATNN N                      701
```

(2) INFORMATION FOR SEQ ID NO: 2:

(i) SEQUENCE CHARACTERISTICS:
      (A) LENGTH: 167 amino acids
      (B) TYPE: amino acid
      (D) TOPOLOGY: linear (ii) MOLECULE TYPE: protein
      (A) DESCRIPTION: Murine ob protein (vi) ORIGINAL SOURCE:

(xi) SEQUENCE DESCRIPTION: SEQ ID NO: 2:

```
Met Cys Trp Arg Pro Leu Cys Arg Phe Leu Trp Leu Trp Ser Tyr Leu
 1               5                  10                  15

Ser Tyr Val Gln Ala Val Pro Ile Gln Lys Val Gln Asp Asp Thr Lys
             20                  25                  30

Thr Leu Ile Lys Thr Ile Val Thr Arg Ile Asn Asp Ile Ser His Thr
         35                  40                  45

Gln Ser Val Ser Ala Lys Gln Arg Val Thr Gly Leu Asp Phe Ile Pro
     50                  55                  60

Gly Leu His Pro Ile Leu Ser Leu Ser Lys Met Asp Gln Thr Leu Ala
65                  70                  75                  80
```

-continued

```
Val Tyr Gln Gln Val Leu Thr Ser Leu Pro Ser Gln Asn Val Leu Gln
                85                  90                  95

Ile Ala Asn Asp Leu Glu Asn Leu Arg Asp Leu Leu His Leu Leu Ala
            100                 105                 110

Phe Ser Lys Ser Cys Ser Leu Pro Gln Thr Ser Gly Leu Gln Lys Pro
            115                 120                 125

Glu Ser Leu Asp Gly Val Leu Glu Ala Ser Leu Tyr Ser Thr Glu Val
            130                 135                 140

Val Ala Leu Ser Arg Leu Gln Gly Ser Leu Gln Asp Ile Leu Gln Gln
145                 150                 155                 160

Leu Asp Val Ser Pro Glu Cys
                165
```

(2) INFORMATION FOR SEQ ID NO: 3:

(i) SEQUENCE CHARACTERISTICS:
        (A) LENGTH: 701 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Mus musculus (xi) SEQUENCE DESCRIPTION: SEQ ID NO: 3:

```
NNNGNNGTTG CAAGGCCCAA GAAGCCCANN NTCCTGGGAA GGAAAATGCA TTGGGGAACC     60
CTGTGNCGGA TTCTTGTGGC TTTGGCCCTA TCTTTTCTAT GTCCAAGCTG TGCCCATCCA    120
AAAAGTCCAA GATGACACCA AAACCCTCAT CAAGACAATT GTCACCAGGA TCAATGACAT    180
TTCACACACG CAGTCAGTCT CCTCCAAACA GAAAGTCACC GGTTTGGACT TCATTCCTGG    240
GCTCCACCCC ATCCTGACCT TATCCAAGAT GGACCAGACA CTGGCAGTCT ACCAACAGAT    300
CCTCACCAGT ATGCCTTCCA GAAACGTGAT CCAAATATCC AACGACCTGG AGAACCTCCG    360
GGATCTTCTT CACGTGCTGG CCTTCTCTAA GAGCTGCCAC TTGCCCTGGG CCAGTGGCCT    420
GGAGACCTTG GACAGCCTGG GGGGTGTCCT GGAAGCTTCA GGCTACTCCA CAGAGGTGGT    480
GGCCCTGAGC AGGCTGCAGG GTCTCTGCA GGACATGCTG TGGCAGCTGG ACCTCAGCCC    540
TGGGTGCTGA GGCCTTGAAG GTCACTCTTC CTGCAAGGAC TNACGTTAAG GGAAGGAACT    600
CTGGTTTCCA GGTATCTCCA GGATTGAAGA GCATTGCATG GACACCCCTT ATCCAGGACT    660
CTGTCAATTT CCCTGACTCC TCTAAGCCAC TCTTCCAAAG G                       701
```

(2) INFORMATION FOR SEQ ID NO: 4:

(i) SEQUENCE CHARACTERISTICS:
        (A) LENGTH: 167 amino acids
        (B) TYPE: amino acid
        (D) TOPOLOGY: linear (ii) MOLECULE TYPE: protein
        (A) DESCRIPTION: Human Ob protein (vi) ORIGINAL SOURCE:

(xi) SEQUENCE DESCRIPTION: SEQ ID NO: 4:

```
Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
```

```
                  20                  25                  30
Thr Leu Ile Lys Thr Ile Val Thr Arg Ile Asn Asp Ile Ser His Thr
            35                  40                  45
Gln Ser Val Ser Ser Lys Gln Lys Val Thr Gly Leu Asp Phe Ile Pro
        50                  55                  60
Gly Leu His Pro Ile Leu Thr Leu Ser Lys Met Asp Gln Thr Leu Ala
 65                  70                  75                  80
Val Tyr Gln Gln Ile Leu Thr Ser Met Pro Ser Arg Asn Val Ile Gln
                85                  90                  95
Ile Ser Asn Asp Leu Glu Asn Leu Arg Asp Leu Leu His Val Leu Ala
            100                 105                 110
Phe Ser Lys Ser Cys His Leu Pro Trp Ala Ser Gly Leu Glu Thr Leu
        115                 120                 125
Asp Ser Leu Gly Gly Val Leu Glu Ala Ser Gly Tyr Ser Thr Glu Val
        130                 135                 140
Val Ala Leu Ser Arg Leu Gln Gly Ser Leu Gln Asp Met Leu Trp Gln
145                 150                 155                 160
Leu Asp Leu Ser Pro Gly Cys
                165

(2) INFORMATION FOR SEQ ID NO: 5:

(i) SEQUENCE CHARACTERISTICS:
        (A) LENGTH: 166 amino acids
        (B) TYPE: amino acid
        (D) TOPOLOGY: linear (ii) MOLECULE TYPE: protein
        (A) DESCRIPTION: Murine ob protein harboring Gln deletionat
            position 49

(vi) ORIGINAL SOURCE:
        (A) ORGANISM: Murine (xi) SEQUENCE DESCRIPTION: SEQ ID NO: 5:

Met Cys Trp Arg Pro Leu Cys Arg Phe Leu Trp Leu Trp Ser Tyr Leu
 1               5                  10                  15
Ser Tyr Val Gln Ala Val Pro Ile Gln Lys Val Gln Asp Asp Thr Lys
                20                  25                  30
Thr Leu Ile Lys Thr Ile Val Thr Arg Ile Asn Asp Ile Ser His Thr
            35                  40                  45
Ser Val Ser Ala Lys Gln Arg Val Thr Gly Leu Asp Phe Ile Pro Gly
        50                  55                  60
Leu His Pro Ile Leu Ser Leu Ser Lys Met Asp Gln Thr Leu Ala Val
 65                  70                  75                  80
Tyr Gln Gln Val Leu Thr Ser Leu Pro Ser Gln Asn Val Leu Gln Ile
                85                  90                  95
Ala Asn Asp Leu Glu Asn Leu Arg Asp Leu Leu His Leu Leu Ala Phe
            100                 105                 110
Ser Lys Ser Cys Ser Leu Pro Gln Thr Ser Gly Leu Gln Lys Pro Glu
        115                 120                 125
Ser Leu Asp Gly Val Leu Glu Ala Ser Leu Tyr Ser Thr Glu Val Val
        130                 135                 140
Ala Leu Ser Arg Leu Gln Gly Ser Leu Gln Asp Ile Leu Gln Gln Leu
145                 150                 155                 160
Asp Val Ser Pro Glu Cys
                165
```

(2) INFORMATION FOR SEQ ID NO: 6:

(i) SEQUENCE CHARACTERISTICS:
        (A) LENGTH: 166 amino acids
        (B) TYPE: amino acid
        (D) TOPOLOGY: linear (ii) MOLECULE TYPE: protein
        (A) DESCRIPTION: Ob protein harboring Gln deletion at
            position 49

(vi) ORIGINAL SOURCE:
        (A) ORGANISM: Human (xi) SEQUENCE DESCRIPTION: SEQ ID NO: 6:

```
Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Ser Val Ser Ser Lys Gln Lys Val Thr Gly Leu Asp Phe Ile Pro Gly
        50                  55                  60

Leu His Pro Ile Leu Thr Leu Ser Lys Met Asp Gln Thr Leu Ala Val
 65                  70                  75                  80

Tyr Gln Gln Ile Leu Thr Ser Met Pro Ser Arg Asn Val Ile Gln Ile
                85                  90                  95

Ser Asn Asp Leu Glu Asn Leu Arg Asp Leu Leu His Val Leu Ala Phe
            100                 105                 110

Ser Lys Ser Cys His Leu Pro Trp Ala Ser Gly Leu Glu Thr Leu Asp
        115                 120                 125

Ser Leu Gly Gly Val Leu Glu Ala Ser Gly Tyr Ser Thr Glu Val Val
    130                 135                 140

Ala Leu Ser Arg Leu Gln Gly Ser Leu Gln Asp Met Leu Trp Gln Leu
145                 150                 155                 160

Asp Leu Ser Pro Gly Cys
                165
```

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: PCR 5 primer for exon 2G7

(iii) HYPOTHETICAL: NO (iv) ANTI-SENSE: NO (xi) SEQUENCE DESCRIPTION: SEQ ID NO: 7:

CCAGGGCAGG AAAATGTG                                              18

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (primer)
            (A) DESCRIPTION: PCR 3 primer for exon 2G7

(iii) HYPOTHETICAL: NO (iv) ANTI-SENSE: YES (xi) SEQUENCE DESCRIPTION: SEQ ID NO: 8:

CATCCTGGAC TTTCTGGATA GG                                            22

(2) INFORMATION FOR SEQ ID NO: 9:

(i) SEQUENCE CHARACTERISTICS:
            (A) LENGTH: 176 base pairs
            (B) TYPE: nucleic acid
            (C) STRANDEDNESS: double
            (D) TOPOLOGY: linear (ii) MOLECULE TYPE: DNA (genomic)
            (A) DESCRIPTION: exon 2G7

(iii) HYPOTHETICAL: NO (iv) ANTI-SENSE: NO (xi) SEQUENCE DESCRIPTION: SEQ ID NO: 9:

GTGCAAGAAG AAGAAGATCC CAGGGCAGGA AAATGTGCTG GAGACCCCTG TGTCGGGTCC    60

NGTGGNTTTG GTCCTATCTG TCTTATGTNC AAGCAGTGCC TATCCAGAAA GTCCAGGATG   120

ACACCAAAAG CCTCATCAAG ACCATTGTCA NCAGGATCAC TGANATTTCA CACACG       176

(2) INFORMATION FOR SEQ ID NO: 10:

(i) SEQUENCE CHARACTERISTICS:
            (A) LENGTH: 15 amino acids
            (B) TYPE: amino acid
            (D) TOPOLOGY: linear (ii) MOLECULE TYPE: peptide
            (A) DESCRIPTION: putative signal sequence of Murine Ob protein (xi) SEQUENCE DESCRIPTION: SEQ ID NO: 10:

Phe Leu Trp Leu Trp Ser Tyr Leu Ser Tyr Val Gln Ala Val Pro
 1               5                  10                  15

(2) INFORMATION FOR SEQ ID NO: 11:

(i) SEQUENCE CHARACTERISTICS:
            (A) LENGTH: 287 base pairs
            (B) TYPE: nucleic acid
            (C) STRANDEDNESS: double
            (D) TOPOLOGY: circular (ii) MOLECULE TYPE: DNA (plasmid)
            (A) DESCRIPTION: pET-15b expression vector (iii) HYPOTHETICAL: NO (iv) ANTI-SENSE: NO (ix) FEATURE:
            (A) NAME/KEY: T7 promoter
            (B) LOCATION: 20..37

(ix) FEATURE:
            (A) NAME/KEY: lac operator
            (B) LOCATION: 39..64

(ix) FEATURE:
            (A) NAME/KEY: His-Tag
            (B) LOCATION: 123..137

(ix) FEATURE:
            (A) NAME/KEY: Thrombin cleavage site
            (B) LOCATION: 184..196

(xi) SEQUENCE DESCRIPTION: SEQ ID NO: 11:

AGATCTCGAT CCCGCGAAAT TAATACGACT CACTATAGGG GAATTGTGAG CGGATAACAA    60

TTCCCCTCTA CAAATAATTT TGTTTAACTT TAAGAAGGAG ATATACCATG GGCAGCAGCC   120

ATCATCATCA TCATCACAGC AGCGGCCTGG TGCCGCGCGG CAGCCATATG CTCGAGGATC   180

CCGCTGCTAA CAAAGCCCGA AAGGAAGCTG AGTTGGCTGC TGCCACCGCT GAGCAATAAC   240

TAGCATAACC CCTTGGGGCC TCTAAACGGG TCTTGAGGGG TTTTTTG                 287

(2) INFORMATION FOR SEQ ID NO: 12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Murine 5 primer (iii) HYPOTHETICAL: NO (iv) ANTI-SENSE: NO (xi) SEQUENCE DESCRIPTION: SEQ ID NO: 12:

CTTATGTTCA TATGGTGCCG ATCCAGAAAG TC                                  32

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Murine 3 primer (iii) HYPOTHETICAL: NO (iv) ANTI-SENSE: Yes (xi) SEQUENCE DESCRIPTION: SEQ ID NO: 13:

TCCCTCTACA TATGTCTTGG GAGCCTGGTG GC                                  32

(2) INFORMATION FOR SEQ ID NO: 14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Human 5 primer (iii) HYPOTHETICAL: NO (iv) ANTI-SENSE: NO (xi) SEQUENCE DESCRIPTION: SEQ ID NO: 14:

TCTATGTCCA TATGGTGCCG ATCCAAAAAG TC                                  32

(2) INFORMATION FOR SEQ ID NO: 15:

```
    (i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Human 3 primer (iii) HYPOTHETICAL: NO (iv) ANTI-SENSE: Yes (xi) SEQUENCE DESCRIPTION: SEQ ID NO: 15:

TTCCTTCCCA TATGGTACTC CTTGCAGGAA GA                                        32

(2) INFORMATION FOR SEQ ID NO: 16:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (ii) MOLECULE TYPE: cDNA
        (A) DESCRIPTION: Normal splice acceptor site in ob (iii) HYPOTHETICAL: NO (iv) ANTI-SENSE: NO (ix) FEATURE:
        (A) NAME/KEY: Splice acceptor site (with Glutamine)

(xi) SEQUENCE DESCRIPTION: SEQ ID NO: 16:

AG CAG TCG GTA                                                             11
   Gln Ser Val (2) INFORMATION FOR SEQ ID NO: 17:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (ii) MOLECULE TYPE: cDNA
        (A) DESCRIPTION: Abnormal splice acceptor site in ob (iii) HYPOTHETICAL: NO (iv) ANTI-SENSE: NO (ix) FEATURE:
        (A) NAME/KEY: Splice acceptor site  (without Glutamine)

(xi) SEQUENCE DESCRIPTION: SEQ ID NO: 17:

AG CAG TCG GTA                                                             11
       Ser Val (2) INFORMATION FOR SEQ ID NO: 18:

(i) SEQUENCE CHARACTERISTICS:
        (A) LENGTH: 16 amino acids
        (B) TYPE: amino acid
        (D) TOPOLOGY: unknown (ii) MOLECULE TYPE: peptide
        (A) DESCRIPTION: ob peptide (v) FRAGMENT TYPE: internal (vi) ORIGINAL SOURCE:
```

```
        (A) ORGANISM: Murine (xi) SEQUENCE DESCRIPTION: SEQ ID NO: 18:

Val Pro Ile Gln Lys Val Gln Asp Asp Thr Lys Thr Leu Ile Lys Thr
1               5                   10                  15

(2) INFORMATION FOR SEQ ID NO: 19:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide
        (A) DESCRIPTION: ob peptide fragment (v) FRAGMENT TYPE: internal (vi) ORIGINAL SOURCE:
        (A) ORGANISM: Murine (xi) SEQUENCE DESCRIPTION: SEQ ID NO: 19:

Leu His Pro Ile Leu Ser Leu Ser Lys Met Asp Gln Thr Leu Ala
1               5                   10                  15

(2) INFORMATION FOR SEQ ID NO: 20:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide
        (A) DESCRIPTION: ob peptide (v) FRAGMENT TYPE: internal (vi) ORIGINAL SOURCE:
        (A) ORGANISM: Murine (xi) SEQUENCE DESCRIPTION: SEQ ID NO: 20:

Ser Lys Ser Cys Ser Leu Pro Gln Thr Ser Gly Leu Gln Lys Pro Glu
1               5                   10                  15

Ser Leu Asp (2) INFORMATION FOR SEQ ID NO: 21:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide
        (A) DESCRIPTION: ob peptide (v) FRAGMENT TYPE: Carboxyl terminal (vi) ORIGINAL SOURCE:
        (A) ORGANISM: Murine (xi) SEQUENCE DESCRIPTION: SEQ ID NO: 21:

Ser Arg Leu Gln Gly Ser Leu Gln Asp Ile Leu Gln Gln Leu Asp Val
1               5                   10                  15

Ser Pro Glu Cys
        20
```